(12) United States Patent
DiFiore et al.

(10) Patent No.: US 7,347,853 B2
(45) Date of Patent: Mar. 25, 2008

(54) CATHETER WITH REMOVABLE EXTENSION

(75) Inventors: Attilio E. DiFiore, Taylorsville, UT (US); Guy Rome, West Valley, UT (US)

(73) Assignee: C. R. Bard, Inc., Murray Hill, NJ (US)

( * ) Notice: Subject to any disclaimer, the term of this patent is extended or adjusted under 35 U.S.C. 154(b) by 175 days.

(21) Appl. No.: 10/987,647

(22) Filed: Nov. 12, 2004

(65) Prior Publication Data
US 2005/0256461 A1    Nov. 17, 2005

Related U.S. Application Data

(63) Continuation-in-part of application No. 10/844,276, filed on May 12, 2004, now Pat. No. 7,063,685, and a continuation-in-part of application No. 10/844,236, filed on May 12, 2004.

(51) Int. Cl.
*A61M 25/16* (2006.01)

(52) U.S. Cl. .................... 604/537; 604/256

(58) Field of Classification Search ........ 604/246–247, 604/236–237, 249, 256, 30, 33–34, 43, 99.02–99.04, 604/167.03–167.04, 288.03, 323, 533–537, 604/244
See application file for complete search history.

(56) References Cited

U.S. PATENT DOCUMENTS

| | | | |
|---|---|---|---|
| 4,000,739 A | 1/1977 | Stevens | |
| 4,387,879 A | 6/1983 | Tauschinski | |
| 4,424,833 A | 1/1984 | Spector et al. | |
| 4,430,081 A | 2/1984 | Timmermans | |
| 4,436,519 A | 3/1984 | O'Neill | |
| 4,473,067 A | 9/1984 | Schiff | |
| 4,610,665 A | 9/1986 | Matsumoto et al. | |
| 4,626,245 A | 12/1986 | Weinstein | |
| 4,650,472 A | 3/1987 | Bates | |
| 4,673,393 A | 6/1987 | Suzuki et al. | |
| 5,000,745 A | 3/1991 | Guest et al. | |
| 5,053,013 A | 10/1991 | Ensminger et al. | |
| 5,092,857 A | 3/1992 | Fleischhacker | |
| 5,358,490 A | 10/1994 | Henry et al. | |
| 5,643,227 A | 7/1997 | Stevens | |
| 5,749,861 A | 5/1998 | Guala et al. | |
| 5,772,628 A * | 6/1998 | Bacich et al. | .................. 604/43 |
| 5,843,046 A * | 12/1998 | Motisi et al. | ................ 604/256 |
| 6,482,188 B1 | 11/2002 | Rogers et al. | |
| 6,551,283 B1 | 4/2003 | Guo et al. | |
| 6,554,805 B2 * | 4/2003 | Hiejima | ..................... 604/247 |
| 6,575,960 B2 | 6/2003 | Becker et al. | |

(Continued)

FOREIGN PATENT DOCUMENTS

WO    WO 03/033049    4/2003

*Primary Examiner*—Nicholas Lucchesi
*Assistant Examiner*—Theodore J Stigell
(74) *Attorney, Agent, or Firm*—Morrison & Foerster

(57) ABSTRACT

Catheter valve assemblies and methods for connecting catheters and/or providing fluid access to catheters. In one variation, a device comprises a catheter valve assembly and an extension leg unit. The extension leg unit includes lumen inserts for engaging valves positioned within the catheter valve assembly. In another variation, the valve assembly comprises a depressable plunger which may be engaged by an access cannula. Various connectors with integrated valve assemblies are also disclosed.

38 Claims, 16 Drawing Sheets

U.S. PATENT DOCUMENTS

| | | |
|---|---|---|
| 2002/0099326 A1* | 7/2002 | Wilson et al. ................ 604/43 |
| 2003/0098430 A1 | 5/2003 | Leising et al. |
| 2004/0097903 A1 | 5/2004 | Raulerson |
| 2004/0122416 A1 | 6/2004 | Voorhees |
| 2004/0122418 A1 | 6/2004 | Voorhees |
| 2004/0176739 A1 | 9/2004 | Stephens et al. |
| 2004/0193118 A1 | 9/2004 | Bergeron |
| 2005/0113805 A1 | 5/2005 | Devellian et al. |
| 2005/0192537 A1 | 9/2005 | Osborne et al. |

* cited by examiner

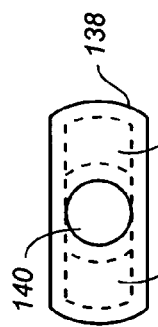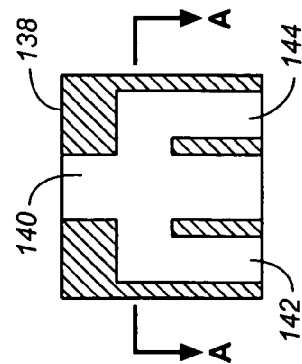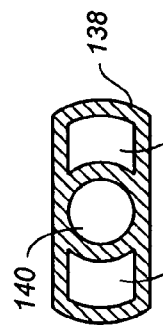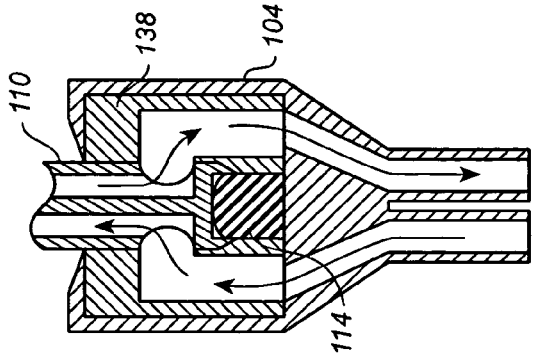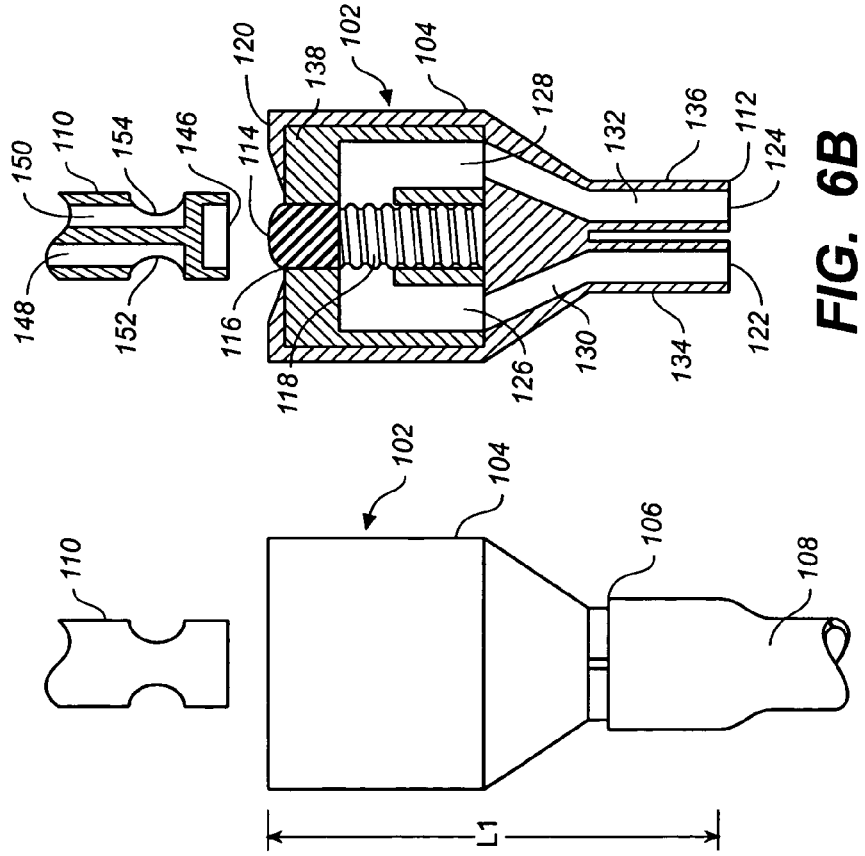

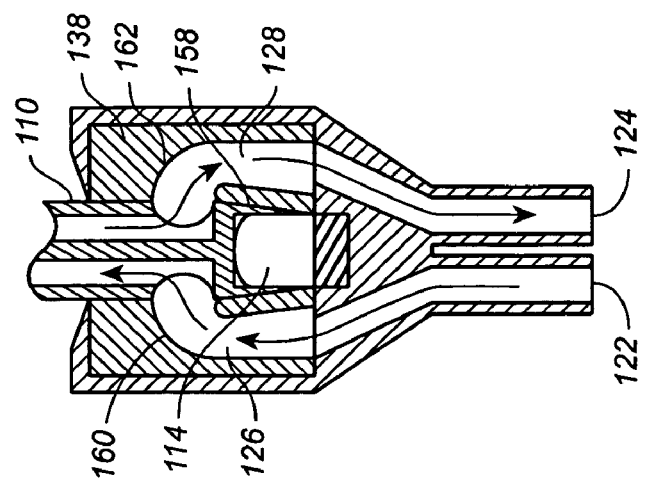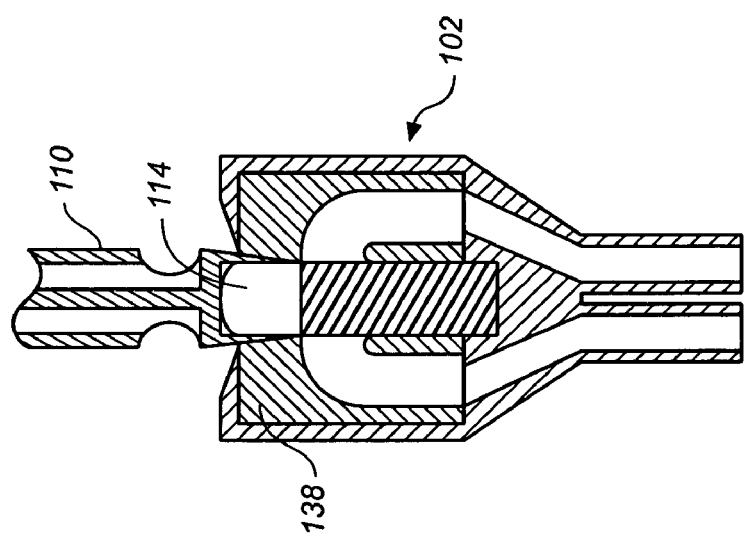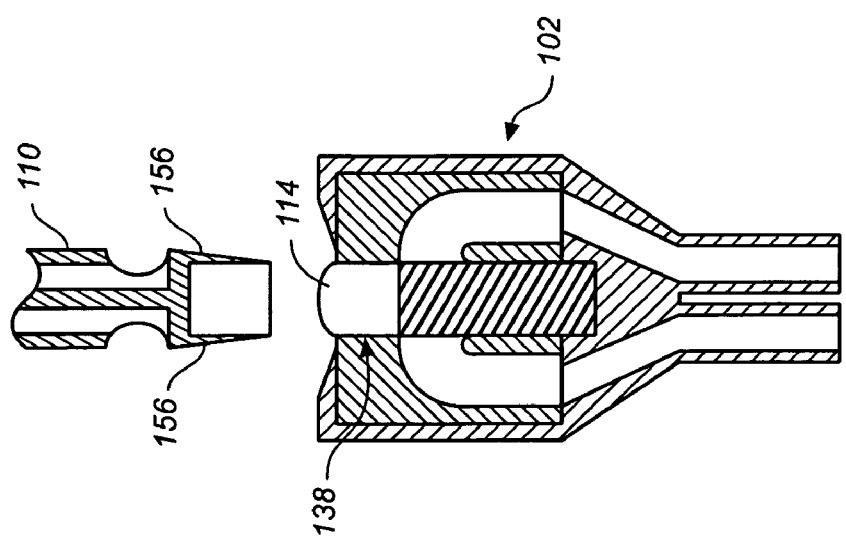

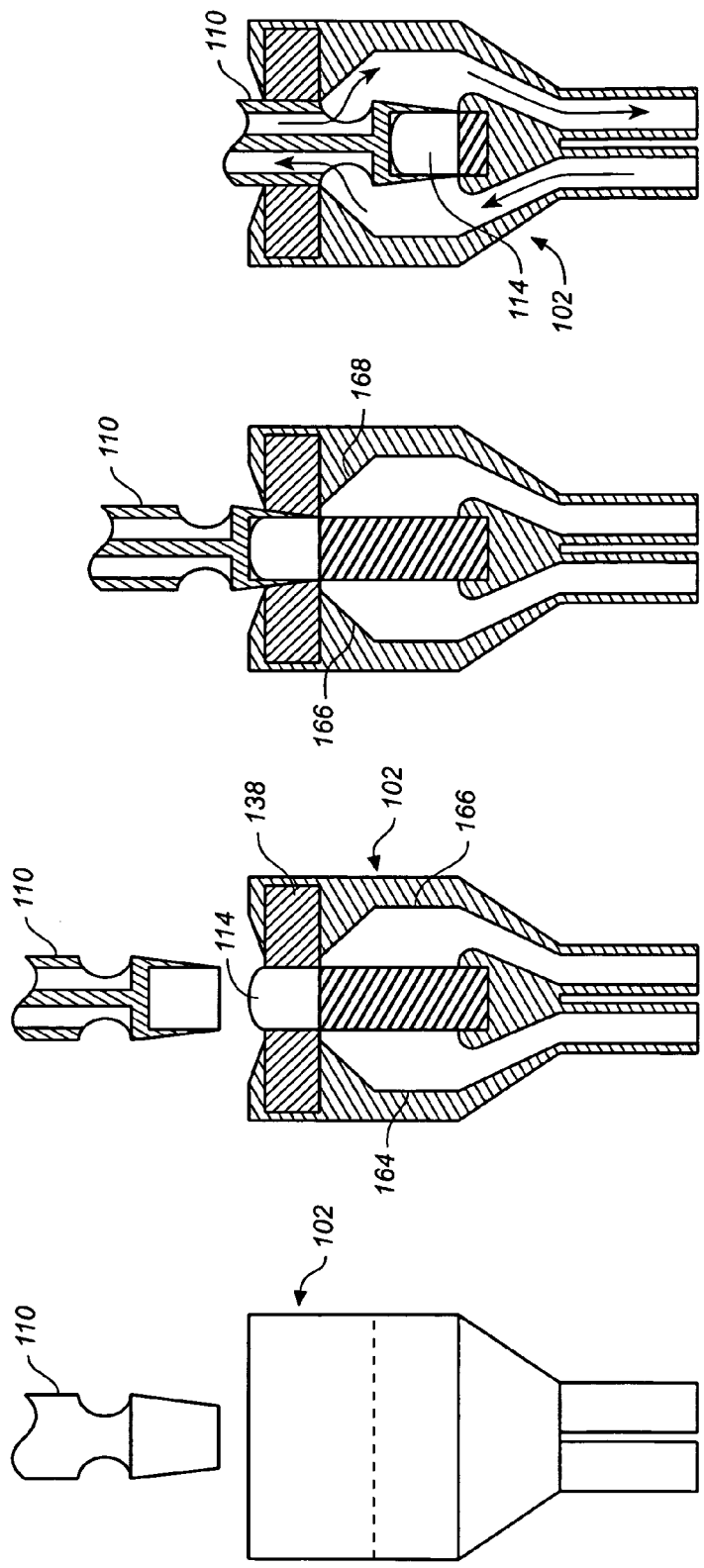

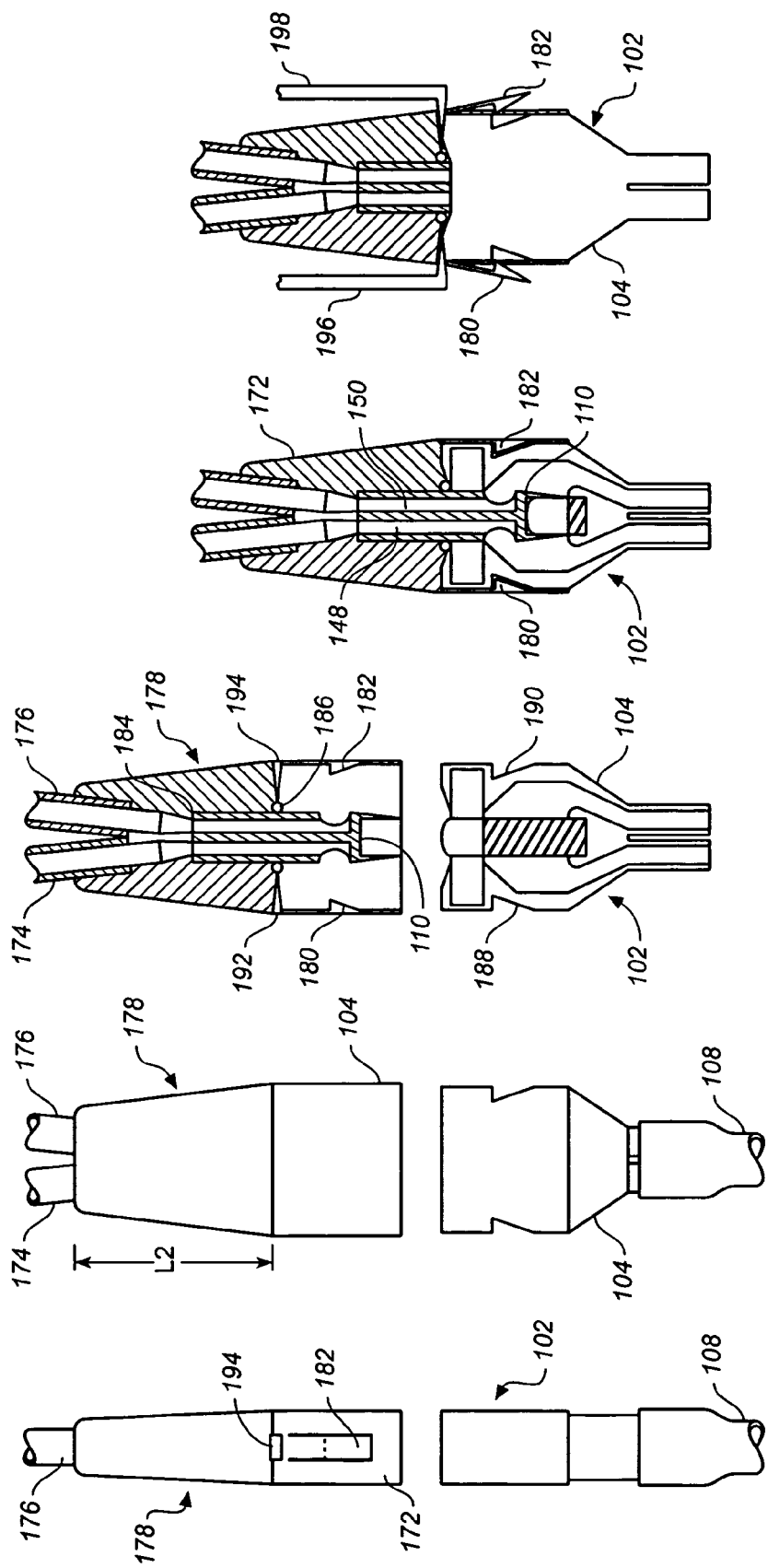

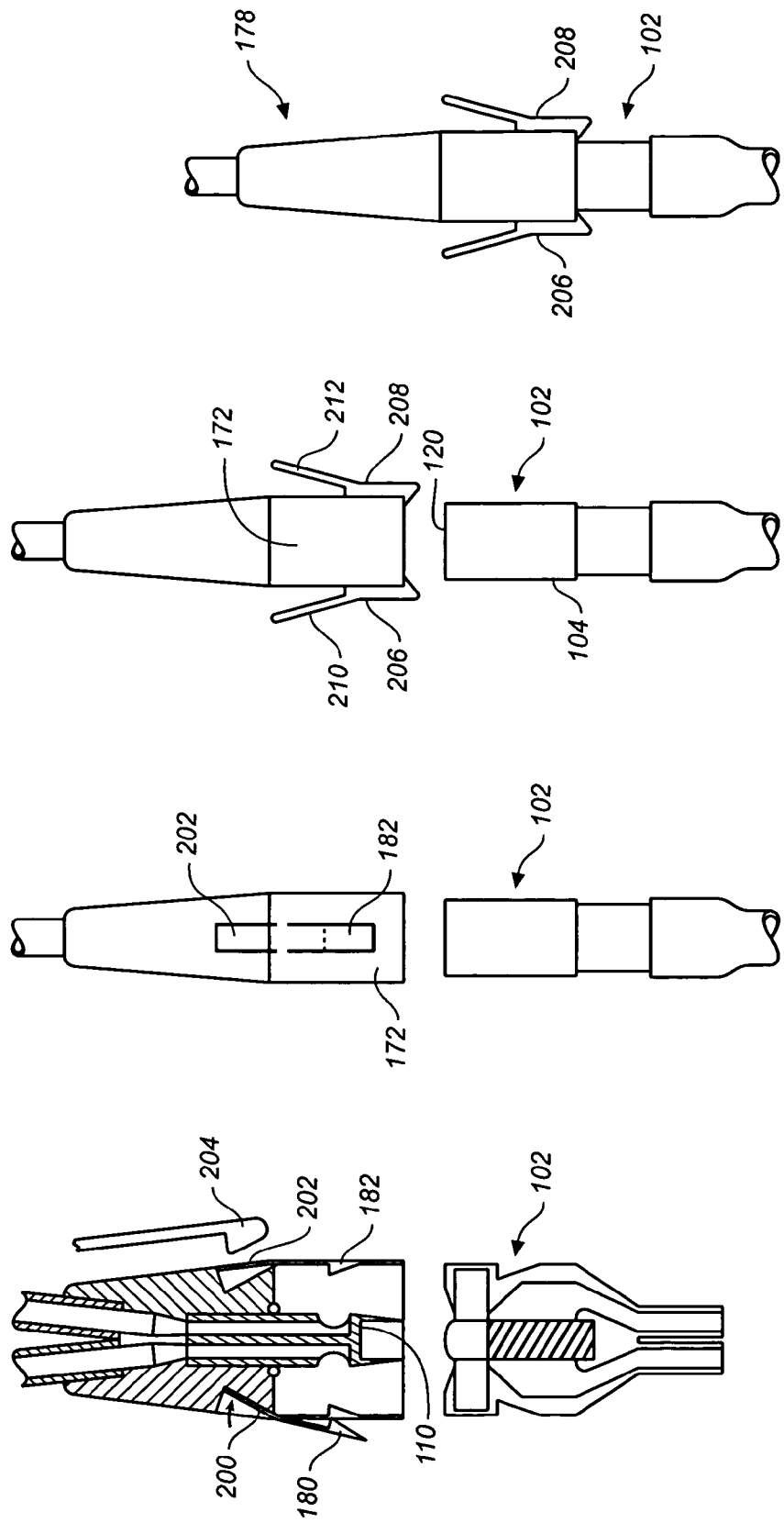

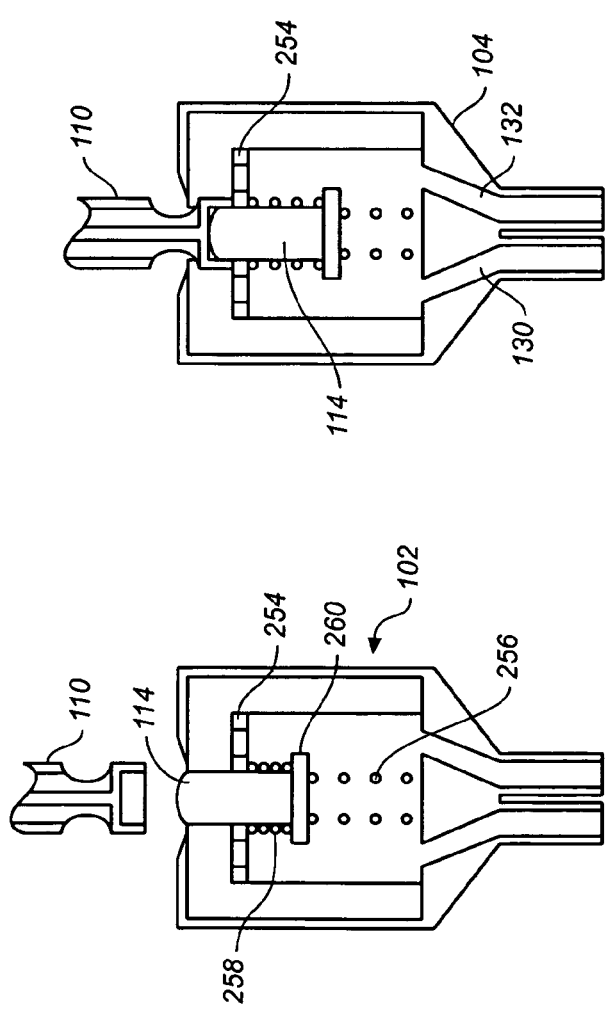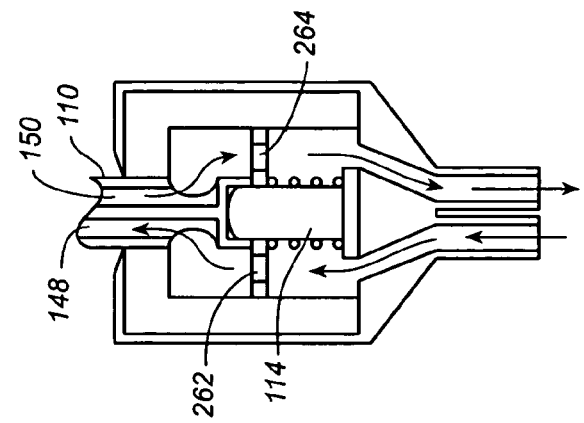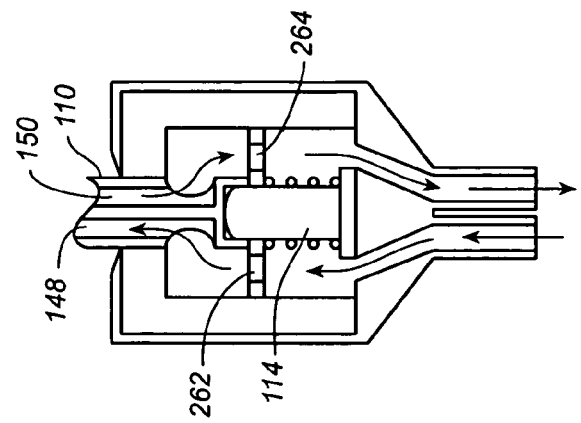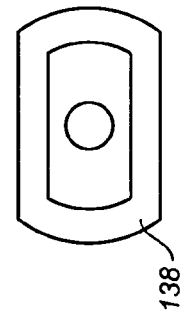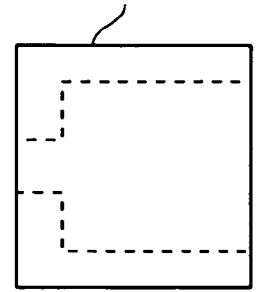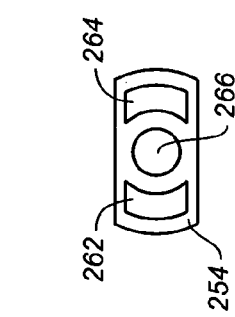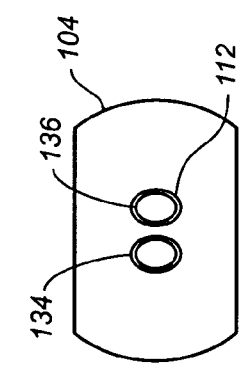
FIG. 14A
FIG. 14B
FIG. 14C
FIG. 14D
FIG. 14E
FIG. 14F
FIG. 14G

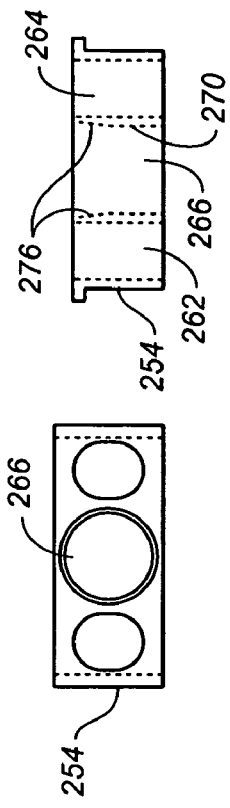
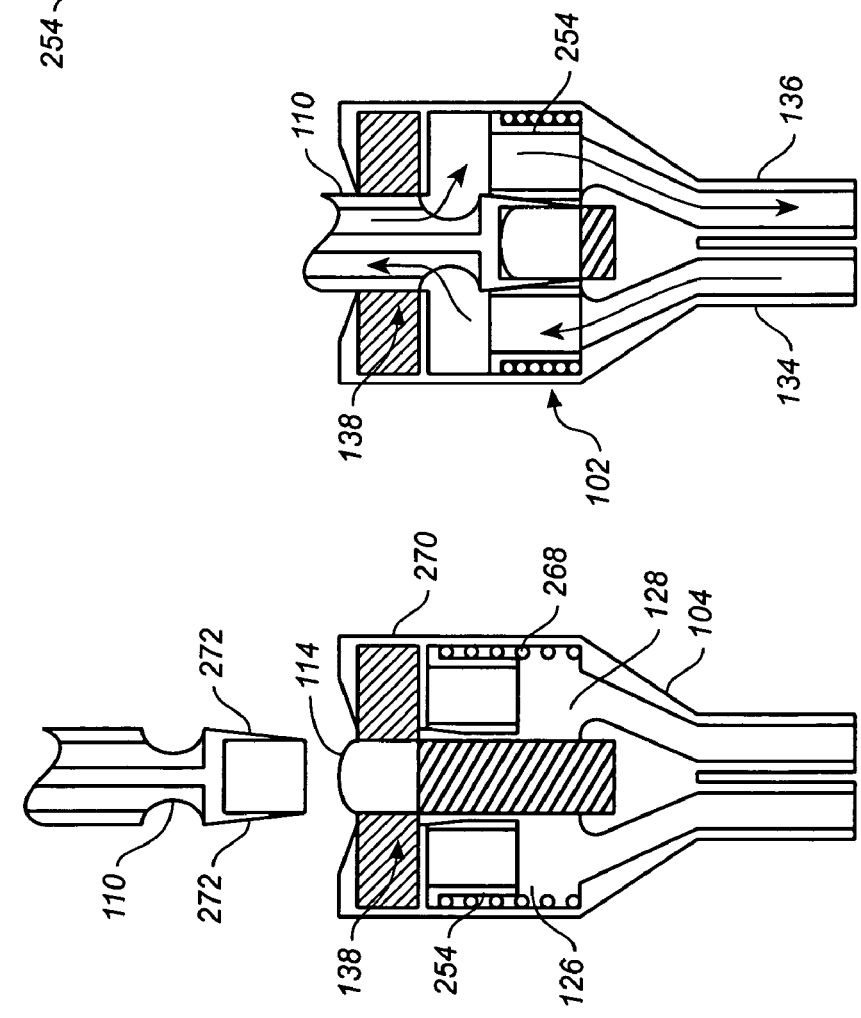

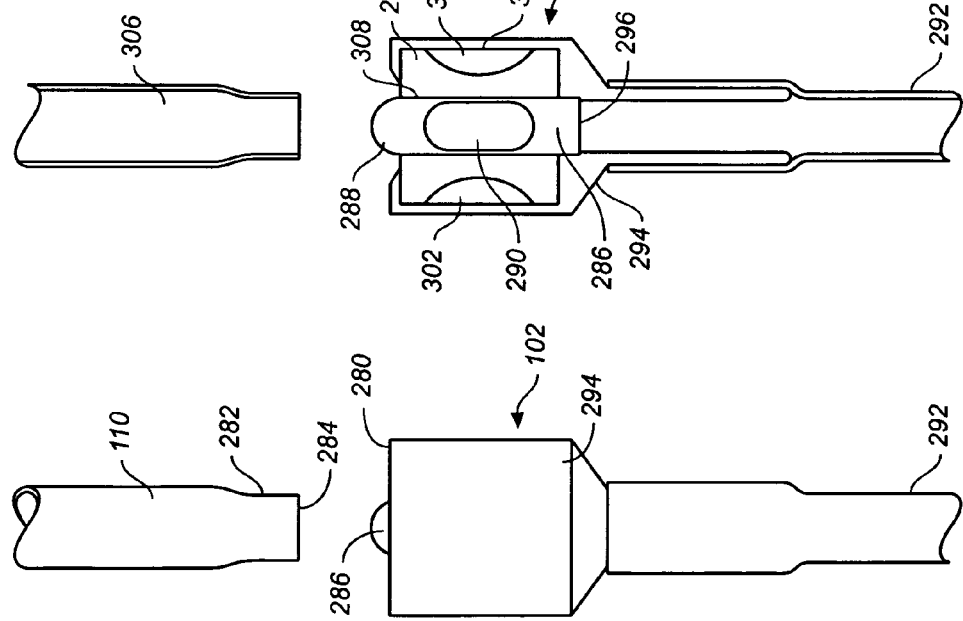
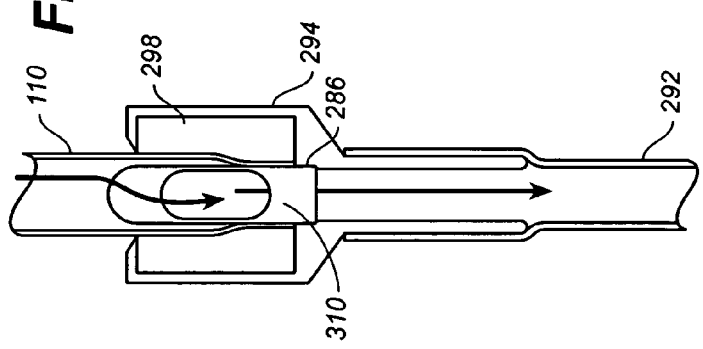
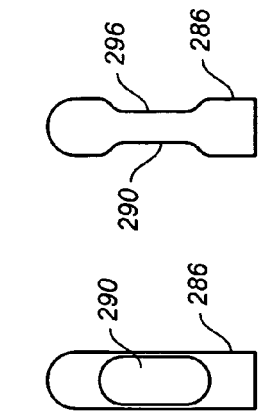
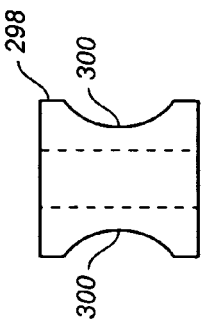

CATHETER WITH REMOVABLE EXTENSION

CROSS-REFERENCE TO RELATED APPLICATIONS

This application is a continuation-in-part of pending U.S. patent application Ser. No. 10/844,236 entitled "Valved Connector" filed May 12, 2004, and a continuation-in-part of U.S. patent application Ser. No. 10/844,276 entitled "Hemostasis Valve for a Catheter" filed May 12, 2004, now U.S. Pat. No. 7,063,685 each of which is incorporated herein by reference in its entirety.

STATEMENT REGARDING FEDERALLY SPONSORED RESEARCH OR DEVELOPMENT

Not applicable.

REFERENCE TO A COMPACT DISK APPENDIX

Not applicable.

BACKGROUND OF THE INVENTION

There are a variety of conditions that require injection of fluids into, or withdrawal of fluids from, a patient's circulatory system. It is common to use an implanted catheter to repeatedly access the patient's vascular system. A flexible guidewire placed in the vascular system may be used to facilitate placement of the catheter, but its use would prevent the physician from capping the proximal end of the catheter to prevent fluid from exiting the catheter or air from entering the vascular system through the catheter during placement. After catheter placement, it is common to attach a valve cap or other terminating device to the proximal end of the catheter to prevent fluid from exiting the catheter or air from entering the vascular system through the catheter. However, in case of accidental separation of the valve cap from the catheter, the distal end of the catheter would then be exposed to the environment outside the body of the patient. The exposed catheter lumen may increase the patient's risk of blood loss, air embolism, or infection.

The use of a cap or adapter to seal the proximal end of a catheter may increase the risk of trapping air pockets within the lumen of the catheter, resulting in an air embolism. Furthermore, during a treatment process requiring infusion of multiple fluids through the implanted catheter, the physician may inadvertently leave the lumens unprotected between procedures, and expose one or more of the lumens to possible contaminations. Thus, an improved catheter access interface may allow easy access to the catheter lumen and at the same time provide better protection against contamination and infection. In addition, an improved catheter access interface may also be configured for utilization as a needle-less access interface for an implanted catheter.

Therefore, a catheter including a self-sealing proximal lumen opening and a corresponding connector for accessing the catheter lumen may be desirable. In particular, a multi-lumen interface with self-sealing mechanisms may be especially desirable in medical procedures where infusion of multiple fluids and/or medications is required.

SUMMARY OF THE INVENTION

Accordingly, described herein is a catheter interconnecting interface that provides a self-sealing capability to the proximal end of a catheter and a corresponding connector for releasing the seal and accessing the catheter lumen. In one aspect of the invention, a multi-lumen catheter is configured with a valve positioned at the proximal opening of each of the lumens. A corresponding connector is provided for opening the valves and providing fluid communication between the catheter lumens and a purity of extension legs on the connector.

In one variation, the catheter device comprises a catheter valve assembly and an extension leg unit. The catheter valve assembly has a proximal opening for receiving a lumen insert on the extension leg unit. The valve in the catheter valve assembly is opened by inserting the lumen insert into the proximal end of the catheter valve assembly, and the valve is closed by retracting the lumen insert from the catheter valve assembly. The catheter valve assembly may be integrated within the proximal end of a catheter. In another variation, the catheter valve assembly comprises a housing with a lumen. The proximal end of the lumen is configured to receive the lumen insert, while the distal end of the housing is configured for connection to a catheter. The catheter may be connected to the housing through a releasable interface. In another variation, a permanent connection may be established between the housing and the catheter.

In another variation, the catheter valve assembly and its corresponding extension leg unit are configured to support a multi-lumen catheter. Each of the lumens in the catheter valve assembly may be provided with a corresponding valve to prevent fluid outflow (i.e., retrograde backflow). A plurality of lumen inserts may be provided on the extension leg unit for opening the valves and providing fluid communication channels to the lumens in the catheter. A plurality of extension legs may extend from the proximal end of the extension leg unit for accessing the lumens in the catheter. In one example, each of the lumens within the catheter is provided with a corresponding extension leg on the extension leg unit, which allows the user to establish fluid communication with each of the lumens independently. Optionally, each of the extension legs may be connected to an extension catheter or tubing. The extension catheters may be attached to the extension leg unit through a removable connection. In another variation, the extension catheters may be permanently connected to the extension leg unit.

In another aspect of the invention, a catheter valve assembly is provided at the proximal end of a catheter to serve as an access interface. In one variation, the catheter valve assembly comprises a housing with a single spring-load valve which actively seals access to one or more chambers in the housing. The catheter valve assembly may be configured to support a catheter including a plurality of lumens. The housing with a single spring-load valve actively seals access to a plurality of chambers in the housing. Each of the chambers is in fluid communication with a corresponding fluid channel. A cannula is provided for interfacing with the valve assembly. The cannula has a plurality of lumens matching the number of chambers in the housing. The cannula is further configured with a sealed distal end, and a side port is provided for each of the lumens. When the cannula is inserted into the housing, the distal end of the cannula displaces the spring loaded valve and establishes fluid communication channels between each of the lumens in the cannula with a corresponding chamber in the housing through the lumen's side port. In another design variation, the catheter assembly with the spring-loaded valve is configured for providing a bifurcating connection to a single lumen catheter. A single lumen cannula with dual side ports is configured for insertion into the valve assembly including two chambers, such that fluid communication can be established between the two chambers in the housing and the single lumen in the cannula.

In yet another aspect of the invention, the catheter valve assembly is configured as a single lumen catheter access system. In one variation, the valve assembly comprises a housing supporting an access tubing. The proximal end of a catheter may be connected to the distal end of the housing such that the lumen of the catheter is in fluid communication with the lumen of the access tubing. The proximal end of the access tubing is closed while one or more orifices are provided on the circumferential surface of the access tubing. Within the housing, a low durometer polymeric material (e.g., silicone, closed cell foam rubber, etc.) surrounds the distal portion of the access tubing and seals the orifices on the access tubing. An access cannula which may be attached to an extension catheter may be provided for interfacing with the access tubing in the housing. When the distal end of the access cannula is inserted into the housing and over the access tubing, the seal around the tubing orifice is displaced, and the proximal portion of the access tubing is positioned within the lumen of the access cannula. The proximal portion of the access cannula has a larger inner diameter than the outer diameter of the access tubing, such that the inner lumen of the access cannula can establish fluid communication with the inner lumen of the access tubing through the tubing orifices. The distal end of the access cannula may be tapered such that it can surround the outer periphery of the access tubing to provide a fluid seal when the access tubing inserted inside the distal lumen of the access cannula.

In addition, methods for establishing fluid communications at the proximal end of a catheter are also disclosed. In one variation, the method comprises inserting lumen inserts into the proximal end of a catheter to displaced valves positioned within the lumens of the catheter. Each of the valves may comprise a unidirectional valve (e.g., duck-bill valve, bi-leaf valve, etc.). The lumen inserts may be connected to a distal end of a housing, with extension legs at the proximal end of the housing for connection to extension tubings. Once the lumen inserts from the housing are inserted into their corresponding lumens at the proximal end of the catheter, fluid communication is established between each of the lumens within the catheters and a corresponding extension leg on the housing. A hemodialysis machine may be connected to the housing through the extension tubings which can be attached to the extension legs. To disconnect the hemodialysis machine from the patient, the operator may simply remove the housing and in the process retract the lumen inserts from the proximal end of the catheter. Once the lumen inserts are removed, the valves within the catheter lumens closes by themselves without further intervention by the operator.

In another variation, the method comprises inserting a cannula into a proximal end of a valve assembly to establish fluid communication with a catheter connected at the distal end of the valve assembly. In one example, the valve assembly comprises a depressible valve, and the cannula includes a blunt distal end for engaging the depressable valve. As the cannula is inserted into the valve assembly, the depressable valve is displaced, and fluid communication is established between the plurality of lumens within the catheter and the plurality of lumens within the cannula. In one variation, the cannula comprises two lumens and each of the lumens has an orifice located on a circumferential surface of the cannula. Insertion of the cannula into the valve assembly establishes fluid communication from each of the cannula lumen through its orifice on the cannula surface to a corresponding catheter lumen. Once the cannula is removed from the valve assembly, the valve closes and seals the proximal end of the catheter.

The implementation of the catheter valve assembly and its corresponding extension leg unit provides various advantages, which may include one or more of the following: (1) the removable extension leg unit may allow the physician to easily disengage multiple fluid infusion lines to a catheter, while simultaneously sealing all access ports without additional efforts; (2) the catheter valve assembly may prevent infection, limit backflow, and minimize embolism by keeping the proximal end of the catheter closed except when accessed by the extension leg unit or the corresponding access cannula; (3) the catheter with the proximal end valve assembly may improve patient safety by insuring that the proximal end of the catheter is closed except when it is properly accessed; (4) the catheter with the valve assembly may be accessed multiple times without requiring replacement; (5) in some variations the catheter valve assembly may allow selective access of individual lumen while keeping the unused lumens sealed; (6) the catheter valve assembly may have built-in safety features to prevent accidental opening of the valve; and (7) because a blood clot begins to form when blood is exposed to air, the automatic closure of the valves immediately upon disengagement of the removable extension leg unit or the access cannula may minimize coagulation within the catheter lumen.

These and other embodiments, features and advantages of the present invention will become more apparent to those skilled in the art when taken with reference to the following more detailed description of the invention in conjunction with the accompanying drawings that are first briefly described.

BRIEF DESCRIPTION OF THE DRAWINGS

FIG. 1 (right) illustrates the corresponding extension leg unit. The extension leg unit comprises a removable bifurcate including two lumen inserts at the distal end for engaging the valves in the catheter valve assembly.

FIG. 6A illustrates one variation of a dual lumen catheter valve assembly, comprising a depressable plunger, and its corresponding blunt cannula for accessing the valve assembly.

FIG. 6B is a cross-sectional view of the valve assembly and its corresponding cannula of FIG. 6A.

FIG. 6C is a cross-sectional view of the valve assembly of FIG. 6A, shown with the cannula depressing the plunger and accessing the valve assembly. One possible fluid flow implementation is illustrated with arrows showing the dual lumen catheter being utilized to support simultaneous inflow and outflow of fluids.

FIG. 6D is a plain view of the septum implemented in the valve assembly of FIG. 6A. The septum is shown from its proximal end, viewed down its longitudinal axis toward its distal end.

FIG. 6E is a cross-sectional view of the septum of FIG. 6D, with the section taken along its longitudinal axis.

FIG. 6F is a cross-sectional view of the septum of FIG. 6E, with the section taken at A-A as indicated in FIG. 6E.

FIG. 7A is a cross-sectional view of another variation of a dual lumen catheter valve assembly, comprising a depressable plunger, and its corresponding blunt cannula for accessing the valve assembly. The valve is shown fully closed.

FIG. 7B illustrates the valve assembly of FIG. 7A with the blunt cannula engaging the plunger of the valve. The valve is shown partially accessed.

FIG. 7C illustrates the valve assembly of FIG. 7A with the valve fully accessed.

FIG. 8A illustrates another variation of a dual lumen catheter valve assembly, comprising a depressable plunger, and its corresponding blunt cannula for accessing the valve assembly.

FIG. 8B is a cross-sectional view of the dual lumen catheter valve assembly of FIG. 8A. The valve is shown fully closed.

FIG. 8C illustrates the valve assembly of FIG. 8A with the valve partially accessed.

FIG. 8D illustrates the valve assembly of FIG. 8A with the valve fully accessed.

FIG. 8E is a plain view of the septum implemented in the valve assembly of FIG. 8A. The septum is viewed from the proximal end towards the distal end.

FIG. 8F is a side view of the septum of FIG. 8E.

FIG. 9A illustrates a side view of one variation of a valve assembly where the accessing cannula is integrated within a housing. The cannula housing is configured to engage the valve assembly housing and property orient the ports on the cannula when the cannula is inserted into the valve assembly.

FIG. 9B is a top view of the valve assembly of FIG. 9A.

FIG. 9C is a cross-sectional view of the valve assembly of FIG. 9B. The access cannula and its supporting housing are shown disengaged from the valve assembly.

FIG. 9D illustrates the valve assembly of FIG. 9C with the access cannula fully engaging the valve.

FIG. 9E illustrates a pair of removal tool being positioned for disengaging the access cannula from the valve assembly.

FIG. 10A illustrates another variation of a valve assembly where the access cannula supporting housing is configured with latches for securing the access cannula unit to the valve assembly housing. An optional removal tool for disengaging the latches is also shown.

FIG. 10B is a side view of the valve assembly and its corresponding access cannula unit of FIG. 10A.

FIG. 11A is a side view of another variation of valve assembly and its corresponding access unit with detachable clips provided for securing the access unit to the valve assembly housing. The access unit is shown separated from the valve assembly.

FIG. 11B shows the valve assembly and the corresponding access unit of FIG. 11A with the access unit engaging the valve assembly. The clips are shown engaging the valve assembly housing and securing the access unit to the valve assembly housing.

FIG. 14A illustrates another variation of a valve assembly with an integrated safety sealing disk. The safety sealing disk prevents air or fluid leak if the sealing plunger is inadvertently depressed. The corresponding access cannula is also shown.

FIG. 14B illustrates the valve assembly of FIG. 13A with the corresponding access cannula engaging the valve assembly. The access cannula is shown in a partially inserted position and engaging both the plunger and the safety sealing disk.

FIG. 14C illustrates the valve assembly of FIG. 13B with the plunger and the safety disk fully depressed, allowing fluids to flow through the valve assembly.

FIG. 14D is a frontal view of the valve assembly of FIG. 14A viewed from the distal end of the valve assembly along the longitudinal axis of the valve assembly towards the proximal end.

FIG. 14E is an end view of the safety sealing disk implemented within the valve assembly of FIG. 14A.

FIG. 14F is a side view of the sealing housing implemented within the valve assembly of FIG. 14A.

FIG. 14G is an end view of the sealing housing of FIG. 14F, shown from the distal end along the longitudinal axis towards the proximal end.

FIG. 15A illustrates yet another variation of a valve assembly with an integrated safety sealing disk. The safety sealing disk prevents air or fluid leak if the sealing plunger is inadvertently depressed. The corresponding access cannula is also shown.

FIG. 15B shows the valve assembly of FIG. 15A with its corresponding access cannula engaging the plunger and the safety sealing disk to keep the valve open for fluid flow.

FIG. 15C is an end view of the safety sealing disk implemented within the valve assembly of FIG. 15A. The safety sealing disk is viewed from the proximal end towards the distal end.

FIG. 15D is a side view of the safety sealing disk of FIG. 15C.

FIG. 15E is an end view of the septum implemented within the valve assembly of FIG. 15A.

FIG. 15F is a side view of the septum of FIG. 15E.

FIG. 16A illustrates another variation of valve assembly supporting single lumen catheter connections. The corresponding access cannula is also shown.

FIG. 16B is a cross-sectional view of the valve assembly of FIG. 16A.

FIG. 16C illustrates the access cannula engaging the valve assembly of FIG. 16B. The valve is opened to allow fluids to flow through the valve assembly.

FIG. 16D is a side view of the of the access tubing of the valve assembly of FIG. 16B.

FIG. 16E is a side view of the access tubing of FIG. 16D with the access tubing rotated 90 degrees along the longitudinal axis of the access tubing.

FIG. 16F is an end view of the sealing housing shown from the proximal end along the longitudinal axis toward the distal end.

FIG. 16G is a side view of the sealing housing of FIG. 16F.

DETAILED DESCRIPTION OF THE INVENTION

Figure 1:
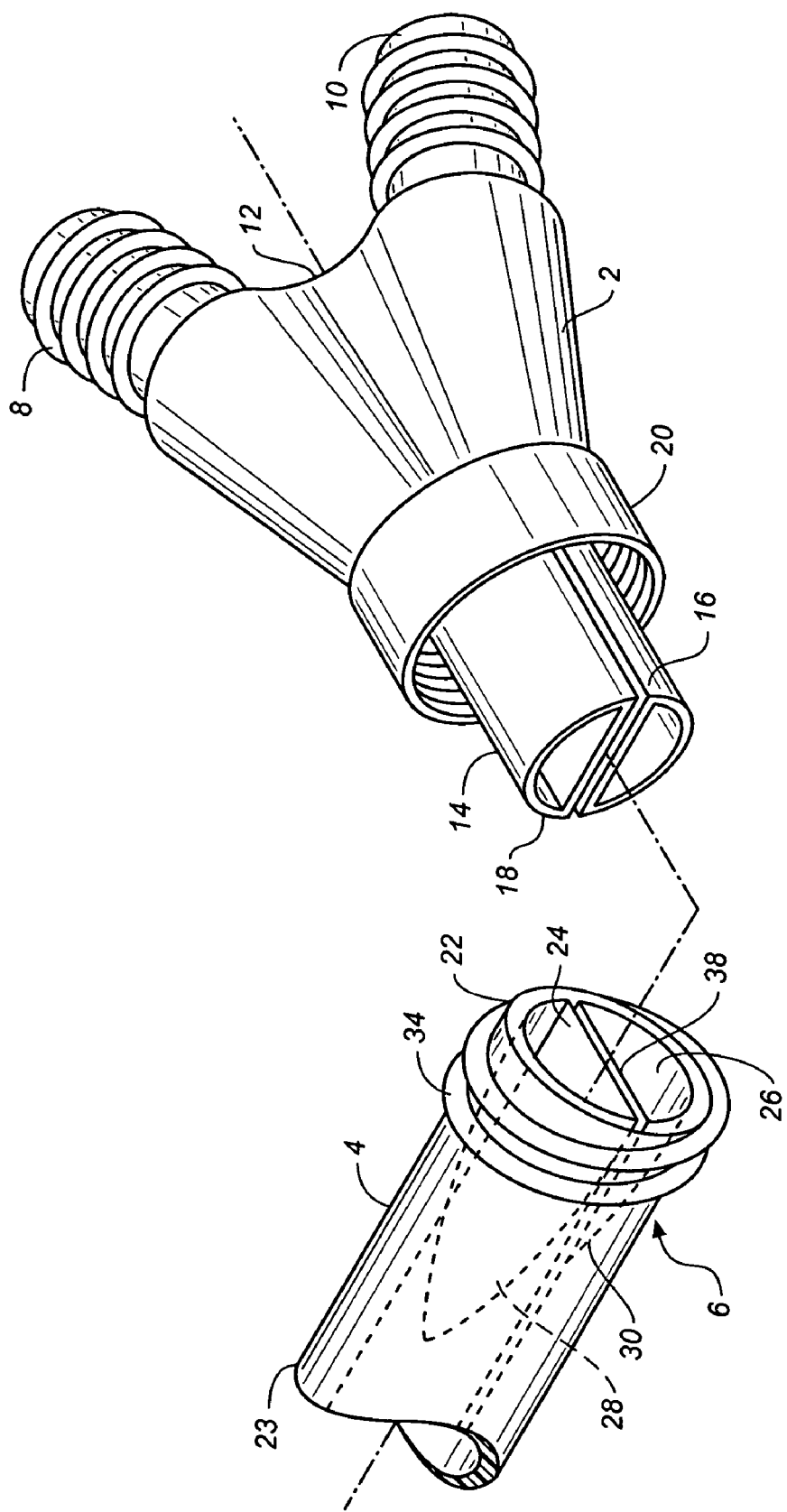
FIG. 1 (left) illustrates the proximal portion of a dual lumen catheter with an integrated valve assembly.

The following detailed description should be read with reference to the drawings, in which like elements in different drawings may be identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

Before describing the present invention, it is to be understood that unless otherwise indicated this invention need not be limited to applications in humans. As one of ordinary skill in the art would appreciate, variations of the invention may be applied to other mammals as well. Moreover, it should be understood that embodiments of the present invention may be applied in combination with various catheters, drug pumps, and infusion devices.

A hemodialysis catheter is used herein as an example application of the extension leg unit with its corresponding valve assembly to illustrate various aspects of the invention disclosed herein. One of ordinary skill in the art having the benefit of this disclosure would appreciate that the valve assembly disclosed herein may be applicable with various catheters for infusion of fluids into the circulatory system in various medical applications. It is also contemplated that the access cannula or extension leg unit with its corresponding valve assembly described herein may be implemented with various fluid infusion lines and catheters, including, but not limited to, hemodialysis catheters, central line catheters and contrast dye injection catheters.

It must also be noted that, as used in this specification and the appended claims, the singular forms "a," "an" and "the" include plural referents unless the context clearly dictates otherwise. Thus, for example, the term "a lumen" is intended to mean a single lumen or a combination of lumens, "a fluid" is intended to mean one or more fluids, or a mixture thereof. Furthermore, the words "proximal" and "distal" refer to directions closer to and away from, respectively, a physician operating the implanted catheter with the tip-end (i.e., distal end) of the catheter inserted inside a patient's body. Thus, for example, the catheter end inserted inside a patient's circulatory system would be the distal end of the catheter, while the catheter end outside the patient's body would be the proximal end of the catheter.

The catheter device with a valve assembly may be used for facilitating the introduction/removal of a fluid into/from a patient's body. The catheter valve assembly may be temporarily attached to the proximal end of the catheter or it may be integrated within the proximal portion of the catheter body. In one aspect of the invention, a removable extension leg unit is implemented for accessing the valve assembly. The distal end of the removable extension leg unit is designed for coupling with the catheter valve assembly at the proximal end of the catheter. The proximal end of the extension leg unit may be coupled to an electromechanically powered and/or magnetically coupled vascular pump to permit assisted flow of a fluid into or out of the patient's body. Bi-directional flow may be achieved with the implementation of multi-lumen catheter.

The catheter valve assembly at the proximal end of the catheter may be configured with an orifice that is large enough to allow the passage of a guidewire and/or introducer (e.g., dilator). Fluid valves, such as polymeric duckbill valves or bi-leaf valves, which are compatible with the guidewire, may be implemented to support "over the guidewire" placement of the catheter. The fluid valves may prevent bleed-back or air embolism during the placement of the catheter. In one design variation, the catheter valve assembly is configured with lumens matching the lumens within the catheter. Each of the lumens within the catheter valve assembly may be configured with a cross-sectional area that is +/−10% of the cross-sectional area of its corresponding catheter lumen. In another variation, each of the lumens within the catheter valve assembly matches the lumen of its corresponding catheter lumen. For example, the valves may be built into the lumen of the catheter.

As is apparent from the figures, the catheter valve assembly at the proximal end of the catheter controls fluid flow into and out of the proximal end of the catheter. In one variation, each of the lumens is configured with a valve. In one particular design, a unidirectional valve (e.g., duck-bill valve, etc.) that allows fluid to flow into the catheter lumen but prevents fluid from flowing out at the proximal end of the catheter is implemented within the valve assembly. The unidirectional valves may be configured such that the physician may selectively inject fluids into one of the plurality of lumens directly without the use of the extension leg unit. The pressure from the injected fluid opens the valve and allows inflow of the fluid. Since the unused lumens are sealed by their corresponding unidirectional valve, the physician does not have to worry about backflow coming out of the unused lumens. In the lumen utilized for fluid injection, once the inflow of the fluid stops, the valve returns to the closed position. The syringe used for fluid injection may have a tip configured to fit into the lumen opening at the proximal end of the catheter valve assembly to provide sealed connection for the injection of the fluid. In another variation, the infusion syringe/instrument may be configured with an extended distal tip that can be inserted into the lumen and through the valve, such that insertion of the extended distal tip forces the valve open. As a result, as long as the extended syringe tip is inserted inside the valve assembly, the valve is kept open, and fluid may be infused or withdrawn by the syringe. Once the syringe is removed, the valve closes.

To utilize the plurality of lumens in the catheter simultaneously, an extension leg unit is provided for engaging the valve assembly. The extension leg unit may be provided with a plurality of lumen inserts for insertion into the catheter valve assembly at the proximal end of the catheter. The lumen inserts force the valves open and establishes fluid inflow/outflow pathways for each of the lumens in the catheter. The valves within the catheter valve assembly may comprise duck-bill valves, bi-leaf valves, spring-loaded valves, etc. For example, the valve can be a spring-like biasing mechanism that is coupled to a luer fitting at the proximal end of the catheter valve assembly. When a corresponding extension leg unit is attached to the catheter valve assembly, the pressure from the insertion of the extension leg unit is transferred to the spring, opening the valve. In the default position, with the extension leg unit disengaged, the valve is biased in the closed position by the spring.

As discussed earlier, unidirectional valves may be advantageous in some applications. In the default state (i.e., extension leg unit not connected), the unidirectional valves prevent fluids from exiting the proximal end of the catheter but allow fluid inflow. When the extension leg unit is connected, the unidirectional valves are kept open and fluid may flow in either direction. For example, the valve may comprise a duck-bill valve that opens when the lumen insert at the distal end of the extension leg unit is inserted into the mouth of the duck-bill valve and forces the two valve leafs to part laterally. The valve may include silicone or other polymeric materials.

In another variation, bidirectional valves that are configured to resist low fluid pressure in the lumen of the catheter and can be forced open through the insertion of lumen inserts may also be utilized. For example, a silicone barrier with one or more pre-cut slit may be implemented as a valve within the valve assembly. The elasticity of the silicone can resist the normal fluid pressure within the catheter lumen and prevent fluid backflow. When the extension leg unit is attached to the catheter valve assembly, the lumen insert pushes through the slit within the silicone barrier and forms a flow-path through the barrier.

Figure 2:
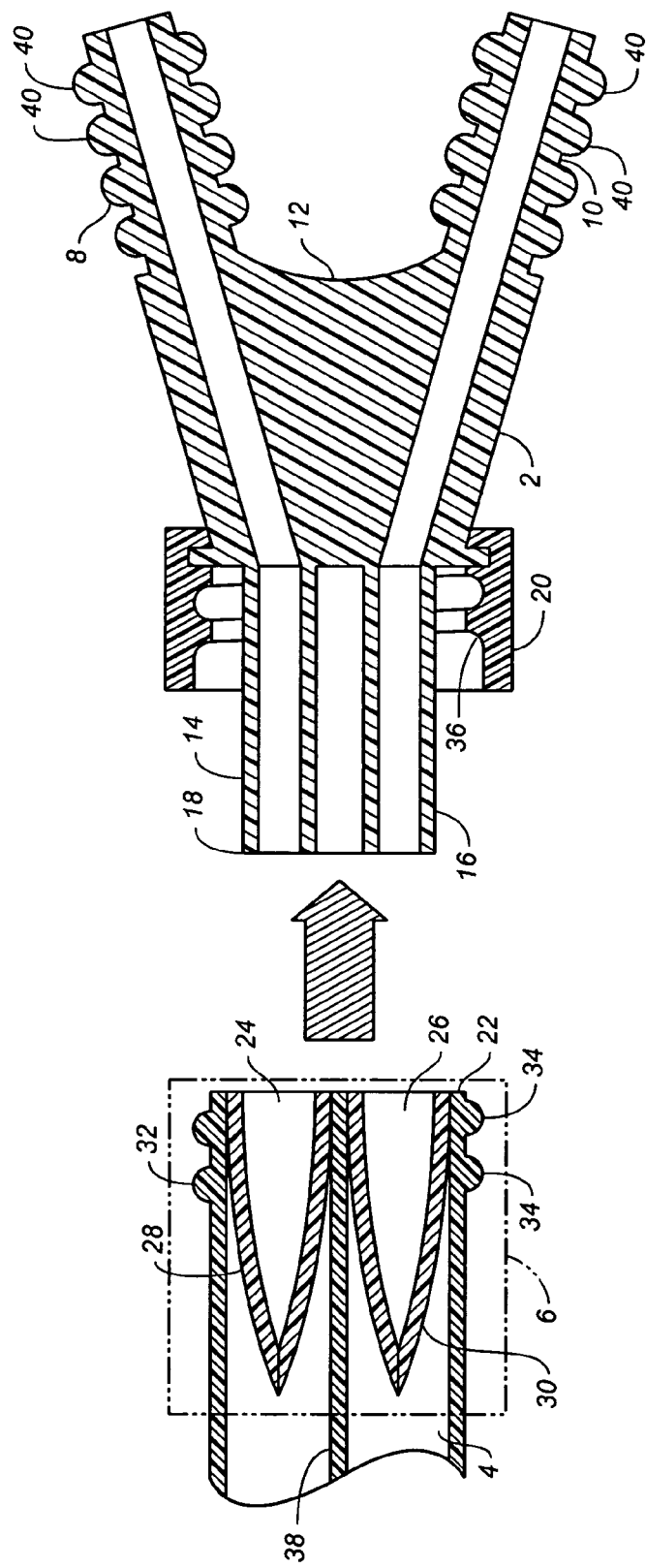
FIG. 2 is a cross-sectional view of the catheter and the corresponding extension leg unit of FIG. 1. The catheter and the extension leg unit are shown in a disengaged position.
Figure 3:
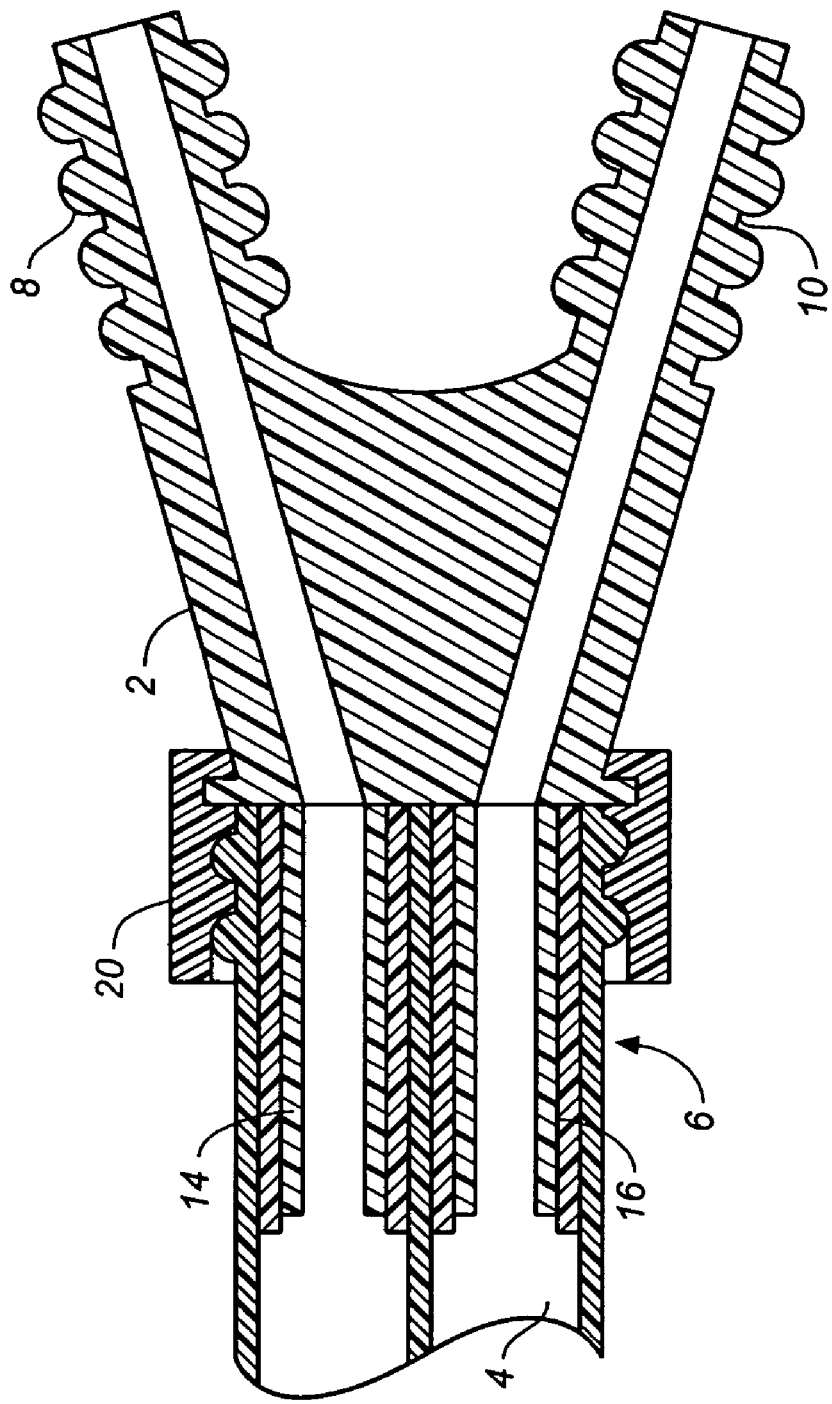
FIG. 3 is a cross-sectional view illustrating the interlocking of the extension leg unit with the catheter. As shown, the lumen inserts engage the valves in the catheter and keep the valves open.

Referring to FIG. 1, one variation of a removable extension leg unit 2 (right side of the figure) and a corresponding catheter 4 with a catheter valve assembly 6 (left side of the figure) are illustrated. In this particular variation, the extension leg unit 2 comprises a removable bifurcate including two extension legs 8, 10 at the proximal end 12 and two lumen inserts 14, 16 at the distal end 18. A luer connector 20 is provided for securing the extension leg 2 unit to the proximal end 22 of the catheter 4. The catheter valve assembly 6 is integrated within the proximal portion of the dual lumen catheter 4. Within each of the catheter lumen 24, 26 is a fluid valve 28, 30 positioned close to the proximal opening. In this particular design, each of the fluid valves 28, 30 comprises a duck-bill valve as shown in FIG. 1. FIG. 2 is a cross-sectional view of the extension leg unit 2 and the catheter 4 of FIG. 1. The catheter valve assembly 6 and the extension leg unit 2 can be engaged by inserting the lumen inserts 14, 16 into the lumens 24, 26 of the catheters, as shown in FIG. 2. FIG. 3 shows the extension leg unit 12 engaged to the catheter 4 via the valve assembly 6. As shown, each of the two lumen inserts 14, 16 diverts the leaflets of the corresponding valve towards the inner wall of the catheter lumen and establishes a continuous fluid pathway from the lumen 24, 26 of the catheter, through the valve 28 30, and into the corresponding extension leg 8, 10. In one embodiment, the catheter valve assembly 6 is configured for repeated and/or prolonged access and does not interfere with fluid flow when valves are opened. In the particular variation shown in FIG. 3, the lumen inserts 14, 16 isolate the valves 28, 30 from the fluid and prevent the valves 28, 30 from interfering with the fluid flow in any way.

In this variation, the luer connector 20 is provided around the distal end of the extension leg unit 2, and corresponding luer interface 32 is provided around the shaft of the catheter 4 at the proximal end of the catheter. The luer connector 20 provides for protection against accidental disconnection of the extension leg unit 2 from the proximal end of the catheter 4. The luer connector 20 can be rotated around the lumen inserts 14, 16, such that once the lumen inserts 14, 16 are inserted into the proximal end 22 of the catheter 4, the luer connector 20 can be rotated to engage the corresponding thread 34 on the circumferential surface at the proximal end of the catheter body 4. The luer connector fits axially about the distal portion of the extension leg unit 2. The inner surface of the luer connector 36 is appropriately threaded such that it can be selectively attached to the threaded portion 34 of the catheter body 4 to secure the catheter 4 to the extension leg unit 2. As illustrated in FIG. 1, the luer connector 20 may include female threads to selectively receive the male threads formed around the shaft of the catheter.

In another variation, the catheter device may further comprise a coupling lock that detachably locks the proximal end of the extension leg set to the catheter valve assembly. In one embodiment, the coupling lock is integrally connected to the extension leg unit and/or the catheter shaft. While FIGS. 1-3 show the luer connector on the extension leg unit, the position of the luer connector may be reversed such that the male side of the luer interface can be on proximal end of the catheter and the female side of the luer interface can be on the extension leg unit.

The catheter device described herein may also include a compression sleeve that fits axially about the distal portion of the extension leg unit around the lumen inserts, as well as fitting axially about each of the extension legs. The compression sleeve may be formed of malleable material so as to provide further compression on the connection between the connecting catheter/tubing and its corresponding connector. For example, luer connection and the compression sleeve may be implemented together to create a force to prevent inadvertent separation of the extension catheter or tube from the extension leg after the extension leg has been inserted into the lumen of the extension catheter/tubing. In another variation, the compression sleeve may be placed on the multi-lumen catheter to secure the catheter on the lumen inserts.

In one embodiment, the catheter has a first and second lumen 24, 26 as shown in FIG. 1. Each of the first and second lumens 24, 26 has a generally D-shaped cross-section. A longitudinally extending wall 38 defines the two lumens 24, 26 along the length of the catheter body 4. Each lumen 24, 26 connect to a respective lumen insert 14, 16 for fluid communication therewith. As shown in FIG. 2, the connection between the proximal portions of each of the extension leg 8, 10 and the distal portion of an extension catheter or tubing is an overlapping fitted connection. However, any other appropriate fastening means, such as detents may be used. In another variation, the proximal end of each leg extension is configured with a female luer interface for connection to an extension tubing's male luer distal tip. In addition, ribs 40 or grooves may be provided on the circumferential surface of the leg extension 8, 10 to improve connection between the leg extensions and their corresponding extension tubings.

Markings, indicators and/or coloring may be provided on the extension leg unit and the proximal portion of the catheter to assist the operator in matching the proper connections between each of the lumen inserts and its corresponding lumen within the catheter. To further ensure matched correspondence, the catheter tips at the proximal end of the catheter, the lumen inserts, and the extension legs may follow the same marking pattern. Thus, the first indicator is associated with one of the lumen inserts and a second indicator is associated with the other lumen insert, such that the first indicator and the second indicator define a correspondence between that lumen insert and an associated catheter lumen. In addition, the corresponding leg extension may be provided with the same indicator. While the indicator may be a visual indicator, such as color or lettering, a multi-lumen catheter with an extension leg attachment utilizing any indicator, visual, tactile, or otherwise, should be considered within the scope of the invention.

For example, the catheter may be a dialysis catheter with staggered lumen openings at the distal end of the catheter. One may provide blue and red markings on the catheter body corresponding to the lumens representing the arterial-line and the venous-line in the dialysis catheter. The lumen inserts and the extension legs on the extension leg unit may also be correspondingly marked with red and blue to prevent the operator from accidentally connecting the venous feed from the dialysis machine to the arterial-line on the catheter.

Figure 4:
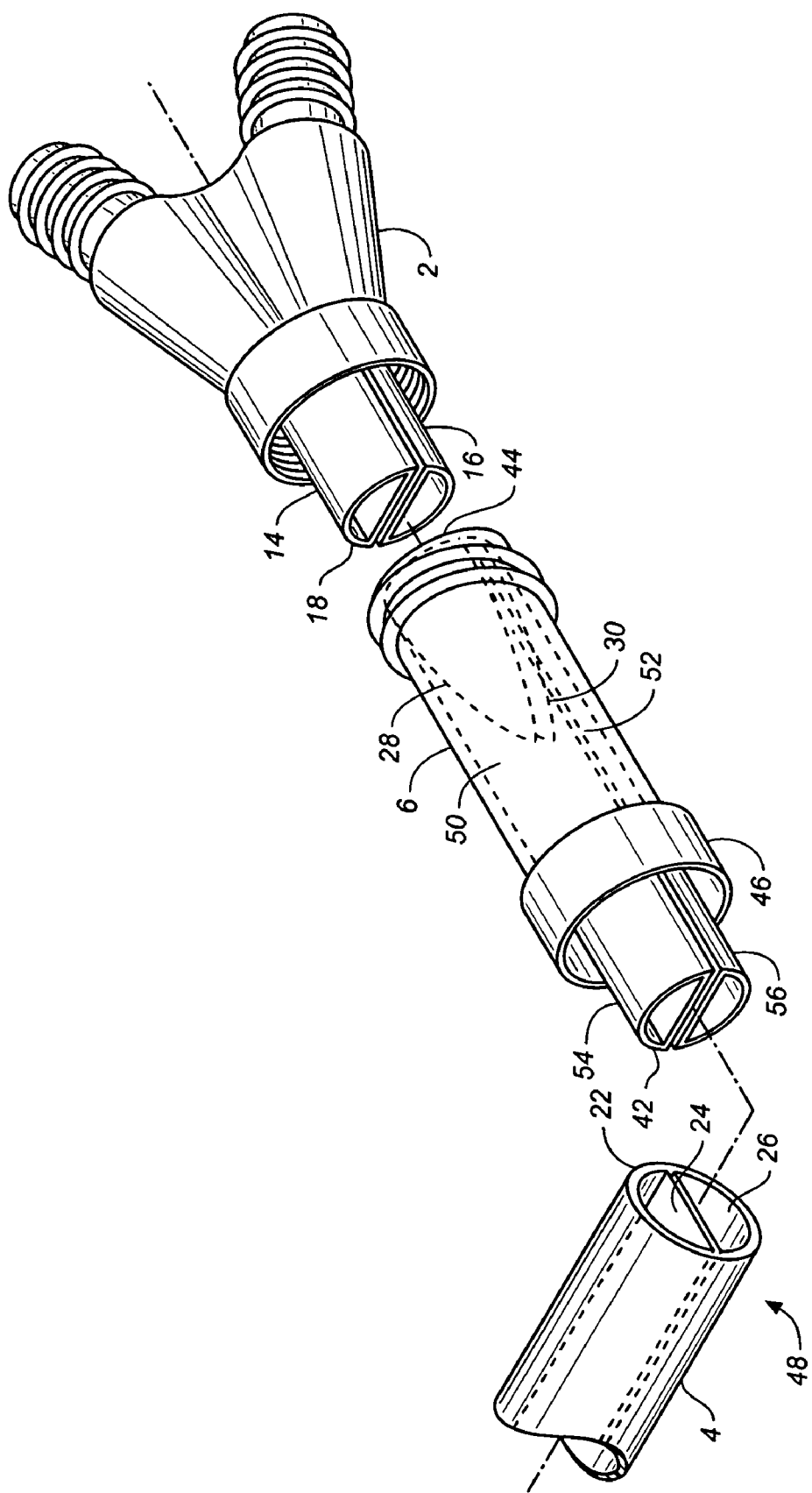
FIG. 4 illustrates another variation where the catheter valve assembly is configured as a separate unit for connection to the proximal end of a catheter to control flow and provide the interface to an extension leg unit.

In another aspect of the invention, the catheter device comprises a catheter valve assembly 6 with a distal end 42 for connection to the proximal end 22 of a catheter 4, and a proximal end 44 for connection to the distal end 18 of an extension leg unit 2, as shown in FIG. 4. The distal end 42 of the catheter valve assembly 6 may comprise an oversleeve 46 for receiving the distal portion 48 of the catheter 4 and allowing the catheter 4 to be solvent-bond to the distal end of the catheter valve assembly 6. In another variation, the distal end 42 of the valve assembly 6 may comprise various locking interfaces with corresponding locking interfaces provided on the proximal end 22 of the catheter 4 for connecting the catheter 4 to the valve assembly 6. In the particular variation shown in FIG. 4, the catheter valve assembly 6 supports two lumens 50, 52. The distal end of each lumen exits in a corresponding lumen insert 54, 56 configured for insertion into one of the lumens 24, 26 at the proximal end 22 of the catheter 4. Although semi-circular lumen shapes are illustrated here, one of ordinary skill in the art would appreciate that other geometries may also be implemented within the corresponding lumens. The proximal ends 44 of the catheter valve assembly 6 are configured to receive the lumen inserts 14, 16 from the extension leg unit 2. A valve 28, 30 is configured within each of the lumens 50, 52 in the catheter valve assembly 6 to prevent retrograde fluid flow when the extension leg unit 2 is disengaged from the catheter valve assembly 6. When the extension leg unit 2 is connected to the proximal end 44 of the catheter valve assembly 6, the lumen inserts 14, 16 from the extension leg unit are inserted into their corresponding lumens 50, 52 in the catheter valve assembly 6, forcing the valves 28, 30 to open. Various locking mechanisms that were described earlier may also be configured here for connecting the extension leg unit 2 to the catheter valve assembly 6. An adapter comprising a valve assembly 6, such as the one illustrated in FIG. 4, may also be implemented for connecting an extension catheter to the proximal end of an implanted catheter.

In another variation, the catheter adapter with an integrated valve assembly may be configured with an antithrombogenic agent and/or an antibacterial agent. An antithrombogenic agent or material may be placed inside the lumens of the adapter to prevent coagulation and formation of thrombus within the adapter. For example, an antithrombogenic agent (e.g., heparinized hydrophilic polymer, various heparin complexes, etc.) may be coated on the inner surface of the adapter's lumens. In another variation, an antibacterial agent or material may be placed within the lumens of the adapter to serve as a bacterial barrier to prevent migration of infective agents into the lumens of an implanted catheter. For example, the adapter may comprise of an antibacterial polymer. In another variation, the inner lumens of the adapter may be coated with an antibacterial agent (e.g., polymer integrated with antibiotic such as gentamicin, nitrofurazone, Minocycline-rifampin, etc.). In anther variation, the polymeric valves within the valve assembly comprise a polymer impregnated with an antithrombogenic and/or an antibacterial agent. Furthermore, an antibacterial agent may also be provided on the outer surface of the adapter.

As stated above, the invention is described with a design containing two lumen inserts and a catheter valve assembly integrated within the tubing at the proximal end of a dual-lumen catheter. The present invention should not be limited, however, to this embodiment. Other appropriate configurations should be considered within the scope of the present invention. For example, the catheter tube and corresponding lumen inserts may be a series of concentric tubes of varying diameter. In another variation, the invention may provide a similar configuration to that described hereinabove with three (or more) lumen inserts and a triple (or more) lumen catheter tube.

Figure 5:
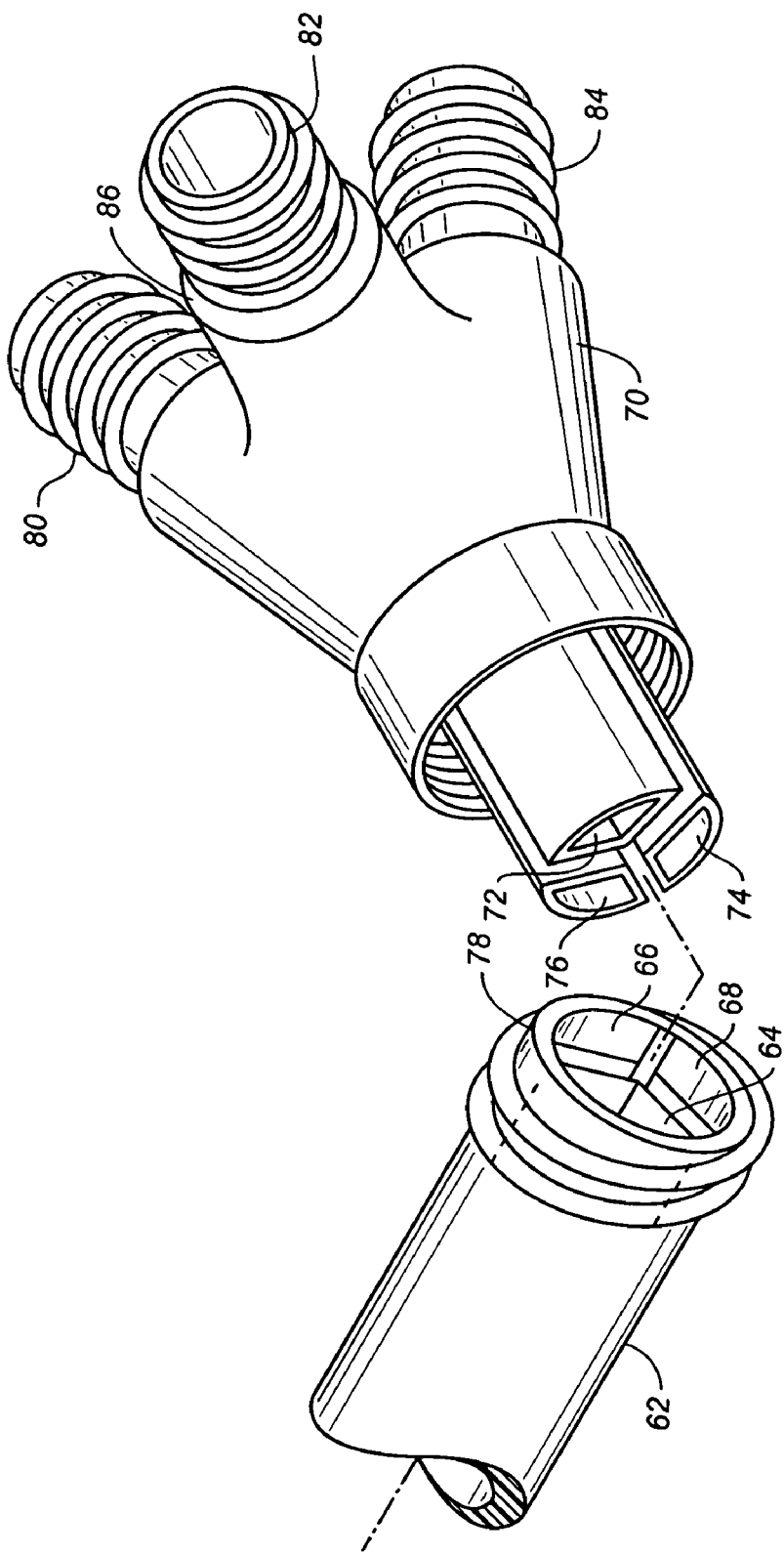
FIG. 5 illustrates yet another variation where the catheter device comprises a triple lumen catheter with a catheter valve assembly integrated within the proximal end of the catheter. A corresponding extension leg unit with three leg extensions for engaging the three lumens at the proximal end of the catheter is also shown.

FIG. 5 illustrates one design variation of a triple lumen configuration. In this variation, the catheter 62 comprises three pie-shaped lumens 64, 66, 68. Each of the catheter lumens 64, 66, 68 has an integrated valve positioned close to its proximal opening. An extension leg unit 70 supporting three lumen inserts 72, 74, 76 is configured for connecting extension tubings to the catheter 62. The three lumen inserts 72, 74, 76 may be placed into the three corresponding lumen openings 64, 66, 68 at the proximal end 78 of the catheter 62. The insertion of the lumen inserts 72, 74, 76 forces the valves in the catheter to open and establishes fluid communication from each of the lumens 64, 66, 68 to one of the three extension legs 80, 82, 84 at the proximal end 86 of the extension leg unit 70. Each of the three leg extensions 80, 82, 84 may be connected to an extension tubing or catheter. In another variation, the triple lumen configuration may be implemented with three circular lumens, instead of the three pie-shaped lumens.

In another variation, the catheter device is configured with fluid valves that allow introduction of an introducer (dilator) and/or guidewire through the catheter device. For example, a duck-bill valve positioned in the lumen of the catheter may be configured to accommodate a dilator. As the dilator is inserted into the proximal end of the catheter, the valve leaf of the duck-leaf valve is forced against the wall of the catheter and allows the dilator to be advanced toward the distal end of the catheter. One of ordinary skill in the art, having the benefit of this disclosure would appreciate that other polymeric valves or compressible/retractable valve mechanisms may also be implemented.

It should be appreciated in view of this disclosure that the catheter device described herein may be configured to permit reverse tunneling of an associated catheter. In the variation shown in FIG. 1, the proximal end 22 of the catheter 4 has a profile similar to the mid-shaft 23 of the catheter 4 such that it can be easily reverse tunneled through a small channel in the body of the patient. In comparison, if the catheter had a large valve mechanism at its proximal end, it would be difficult to pass the proximal end of the catheter with a large surface profile through a small channel created within the body of the patient. In one particular design, the proximal portion of the catheter, which houses the valve assembly, has a cross-sectional area that is no more than 10% larger than the cross-sectional area at the mid-shaft of the catheter body. In another design variation, the proximal portion of the catheter has a cross-sectional area that is no more than 5% larger than the cross-sectional at the mid-shaft of the catheter body.

Because the extension leg unit may comprise low cost polymeric materials, the extension leg unit may be dispensed after one treatment. The use of a new extension leg unit for each treatment may decrease the risk of infection. In some applications, such as chemotherapy treatment, it may be desirable to dispose of the extension leg unit and the associated extension tubings that are connected to the extension legs. Furthermore, blood filters, drug infusion pumps, and other medical instrumentation may be connected to a new extension leg unit prior to connection of the extension leg unit to the catheter, thereby enabling ease of connection of the patient's implanted catheter to a plurality of tubings or fluid sources. For example, the arterial-line and the venous-line of the dialysis machine may be connected to an extension leg unit prior to the patient's arrival. Once the patient is ready, the patient can be quickly hooked up to the dialysis machine by simply connecting the proximal end of the implanted dialysis catheter to the extension leg unit. After treatment, patient may be quickly disconnected from all the tubings by simply disconnecting the extension leg unit from the proximal end of the implanted dialysis catheter. Once the extension leg unit is removed, the valves at the proximal end of the catheter automatically close, and prevent fluid backflow from the catheter and seal the lumens from outside air exposure. An optional cap may then be placed on the proximal end of the implanted dialysis catheter.

In one variation, the extension leg unit may be configured with an antithrombogenic agent and/or an antibacterial agent. An antithrombogenic agent or material may be placed inside the lumens of the extension leg unit to prevent coagulation and formation of thrombus within the extension leg unit. For example, an antithrombogenic agent (e.g., heparinized hydrophilic polymer, various heparin complexes, etc.) may be coated on the inner surface of the extension leg unit's lumens. In another variation, antibacterial agent or material may be placed within the lumens of the extension leg unit to serve as a bacterial barrier to prevent migration of infective agents into the lumen of an implanted catheter. For example, the extension leg unit may comprise of an antibacterial polymer. In another variation, the inner lumens of the extension leg unit may be coated with an antibacterial agent (e.g., polymer integrated with antibiotic such as gentamicin, nitrofurazone, Minocycline-rifampin, etc.). Furthermore, an antibacterial agent may also be provided on the outer surface of the extension leg unit.

In another variation, the catheter device is configured to allow fluids to flow through the catheter device at a flow rate of about 0-500 ml/min. The valves assembly and the corresponding extension leg unit may be configured such that they introduce minimal resistance along the fluid flow paths. In another design, the catheter device is configured to support a fluid infusion rate of at least 200 ml/min. In yet another design, the catheter device is configured to support a fluid infusion rate of at least 400 ml/min.

In yet another variation, the catheter device further comprises a porous mesh or filter positioned along one or more of the fluid paths. In one variation, the porous mesh or filter is positioned in the catheter valve assembly unit. In another variation, the porous mesh or filter is positioned in the extension leg unit. For example, the porous mesh or filter may be placed in the lumen within each of the extension legs. The housing of the extension leg unit may comprise a transparent plastic such that the operator can easily monitor fluid flow inside the extension leg unit. Because the extension leg unit may be disposable, if the porous mesh or filter is clogged, the operator may simply replace the entire extension leg unit.

In another aspect of the invention, the catheter valve assembly 102 is configured within a housing 104 that may be removably or permanently attached to the proximal end 106 of a catheter 108. In one variation, as shown in FIG. 6A, a valve assembly 102 is provided for accessing the proximal end 106 of a dual lumen catheter 108. An access cannula 110 is configured for insertion into a housing supporting a valve assembly. The distal end 112 of the housing 104 is connected to a dual lumen catheter 108. In one particular design, the housing 104 is configured with a length, L1. The valve assembly 102 comprises a depressable plunger. 114 for sealing the opening 116 on the valve assembly 102, as shown in FIG. 6B. In this particular example, the plunger 114 is spring-loaded 118. However, one of ordinary skill in the art would appreciate that other compression mechanisms or resilient materials that can overcome compressive stress may also be utilized in place of a spring 118 to actively displace the plunger 114 to seal the access opening 116 of the valve assembly.

The proximal end 120 of the housing has an opening 116 for receiving an access cannula 110. At the distal end 112 of the housing 104 are two ports 122, 124 for connection to a dual lumen catheter. Within the housing, two chambers 126, 128 are provided. Each of the two chambers 126, 128 is connected to a corresponding port 122, 124 through a channel 130, 132. The proximal end of the housing may be configured with two extension legs 134, 136 for insertion into a dual lumen catheter, such that the catheter may be directly connected to the housing without the need for a standard bifurcation, extension legs and luer connectors.

A septum 138, which may be made of a material such as silicone, is implemented to provide a seal around the plunger 114 when the plunger is in an extended position. FIG. 6D shows the septum 138 from its proximal end. A center opening 140 is provided for receiving the plunger, and two side openings 142, 144 are provided to surround the two chambers. FIG. 6E is a cross-sectional view of the septum 138 taken along its longitudinal axis. FIG. 6F is a cross-sectional view of the septum taken along section A-A as indicated in FIG. 6E. An optional flexible boot or sleeve may be placed around the spring 118 to protect the spring and prevent particle build-up within the gaps within the spring.

An access cannula 110 is provided to depress the plunger 114, allowing fluid access of the chambers 126, 128 within the valve assembly housing 104. The proximal end of the access cannula 110 may be connected to a catheter. In another variation, the distal end of a catheter may be modified to serve as an access cannula. In this example, the access cannula has a blunt distal end 146 for interfacing with the plunger 114. Two lumens 148, 150 are provided within the access cannula. Each of the lumens 148, 150 has a side port 152, 154 such that when the access cannula is inserted within the valve assembly, fluid communication may be established between a corresponding chamber 126, 128 within the housing and the lumens 148, 150 of the access cannula. FIG. 6B shows the valve closed with the access cannula 110 disengaged from the valve assembly 102. FIG. 6C shows the access cannula 110 depressing the plunger 114, which fully opens the valve.

Another variation of the valve assembly 102 is illustrated in FIG. 7A. In this variation, the distal end of the access cannula 110 has a taper 156 to facilitate the insertion of the cannula 110 into the valve assembly 102. The tapered profile may help separate the septum 138 from the plunger 114, as shown in FIG. 7B. When the access cannula 110 is fully inserted into the valve assembly 102, the tapered profile engages the inner wall 158 of the septum 138 and seals the plunger 114 and its spring mechanism from the fluid flowing in the chambers 126, 128 of the valve assembly 102, as shown in FIG. 7C. In this variation, the fluid flow path is defined by the septum 138 that also serves to seal around the plunger 114 when the valve assembly is not accessed. The septum 138 also seals around the access cannula 110 when the valve assembly is accessed. The inner surface 160, 162 of the septum 138 is configured with a curved profile to allow a guidewire inserted from the distal port 122, 124 of the housing to easily pass through the valve assembly 102. For over the guidewire insertion, an adapter with an access cannula may be utilized to depress the plunger and keep the valve open.

Referring to FIGS. 8A-8D, another variation of the valve assembly 102 is illustrated. In this design, the septum 138 has a disk-shaped body with a center opening 140 to accommodate the plunger 114. FIG. 8E shows the septum 138 from a top view. FIG. 8F is a side view of the septum 138. The inner wall 164, 166 of the valve assembly housing surrounds the two chambers 126, 128. The walls 168, 170 at the proximal end of the chambers are tapered to assist the pass-through of a guidewire.

A housing, adapter, or casing 172 may be provided to support the access cannula 110 and to position the access cannula 110 within the valve assembly 102 when the valve assembly 102 is accessed. FIGS. 9A-9E illustrate one variation in which the housing 172 for the access cannula 110 is configured with leg/tubing extensions 174, 176. FIG. 9A is a side view of a detachable extension leg unit 178 for interfacing and accessing the corresponding valve assembly 102. The distal end of the valve assembly housing is connected to a dual lumen catheter 108. Latches 180, 182 are provided for securing the detachable extension leg unit 178 to the housing 104 of the valve assembly 102. FIG. 9B is a top view of the detachable extension leg unit 178 and the corresponding valve assembly. In this particular design, the housing 104 of extension leg unit 178 has a length L2. As shown in FIG. 9C, two extension/tubing 174, 176 are connected to the proximal end 184 of the access cannula 110 and direct fluids in and out of the two lumens 148, 150 within the access cannula 110. The two extensions 172, 176 bifurcate as they exit the housing 172. Luer connectors may be provided at the proximal end of the extensions for connection to other tubing or catheters. In another variation, a single extension with a dual lumen may be implemented on the access cannula housing 172 for connection to the proximal end of the access cannula 110. In addition, an optional redundant O-ring seal 186 may be provided on the shaft of the access cannula 110 to improve the seal between the access cannula 110 and the valve assembly 102 when the access cannula 110 engages the valve assembly 102.

As shown in FIG. 9C, latches 180, 182 are provided on the inner surface of the access cannula housing 172 for engaging and securing the access cannula housing 172 to the valve assembly housing 104. FIG. 9D shows the access cannula 110 fully inserted within the valve assembly 102 and the latches 182, 182 engages their corresponding notches 188, 190 on the valve assembly housing 104. In this particular design, slots 192, 194 are provided on the access cannula housing 172 for receiving a removal tool 196, 198 to release the latches from the valve assembly housing. As shown in FIG. 9E, a pair of removable tools 196, 198 are inserted into the removal tool access slots and the latches 180, 182 are forced to disengage from their corresponding notches 188, 190. Once the latches 180, 182 have disengaged, the detachable extension unit 178 with its access cannula 110 may be pried apart from the valve assembly unit 102.

One of ordinary skill in the art having the benefit of this disclosure would appreciate that various other locking mechanisms may be implemented to secure the access cannula within the valve assembly. In another variation, latches 180, 182 with built-in levers 200, 202, such as the ones illustrated in FIG. 10A may be utilized. An optional removal tool 204 may be provided to disengage the latches 180, 182. FIG. 101B is a side view illustrating the position of an integrated latch 182. In another example, detachable clips 206, 208 may be provided on the housing 172 supporting the access cannula 110, as shown in FIG. 11A. The operator depresses the lever 210, 212 on the clip to release the distal end of the clip so the valve assembly 102 may be slid into the access cannula housing 172. Once the valve assembly 102 is positioned in place, the clips 206, 208 are released to engage the valve assembly housing 104 and secure the proximal end 120 of the valve assembly housing 104 within the access cannula housing 172 as shown in FIG. 11B. To disengage from the valve assembly 102, the operator may depress the clips 206, 208 and pull the access cannula unit 178 off of the valve assembly 102.

Figure 12:
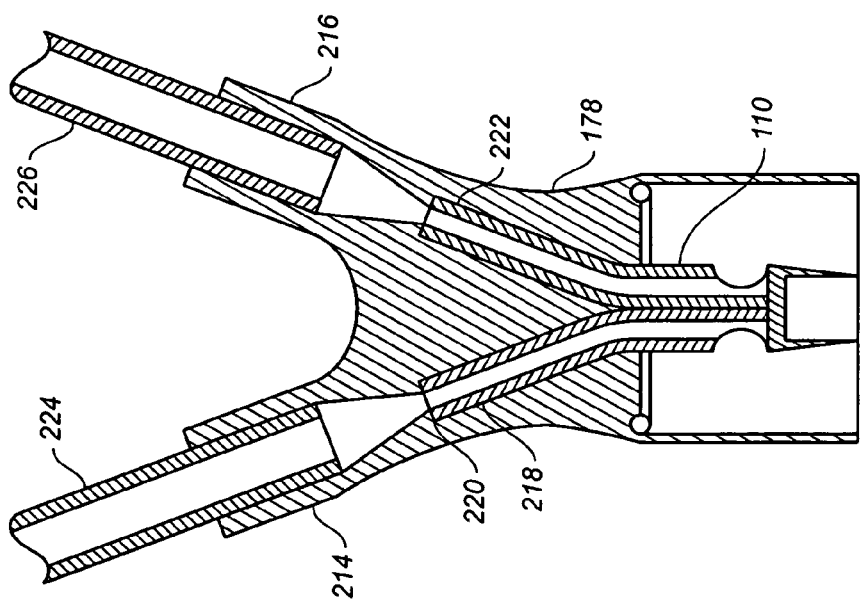
FIG. 12 illustrates another variation of an access unit where the access cannula bifurcates at the proximal end, and the housing supporting the cannula is provided with two channels to supporting fluid communications to two separate catheters that are connected to the proximal end of the cannula housing.

In another variation, the access cannula unit 178 may be configured with extension legs 214, 216 branching from the housing 172, supporting the access cannula, as show in FIG. 12. In this particular design, the proximal portion 218 of the cannula 110 is configured with a bifurcation. Each branch of the bifurcate 220, 222 is connected to a respective lumen of one of the two extension legs 214, 216. Tubing or catheters 224, 226 may be solvent bond onto the extension legs as shown in FIG. 12. In another variation, a luer fitting may be provided at the proximal ends of the extension legs 214, 216 such that tubing or catheters 224, 226 may be connected to the extension legs 214, 216. Certainly, there are many other ways to connect tubing 224, 226 to extension legs 214, 216, which would be within the scope of this invention.

Figure 13B:
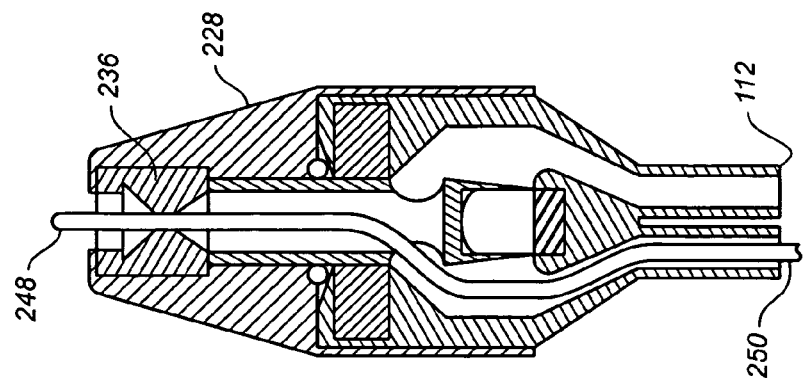
FIG. 13B illustrates the adapter cap of FIG. 13A engaging its corresponding valve assembly. The valve is forced open to allow a guidewire to pass through the valve assembly.
Figure 13A:
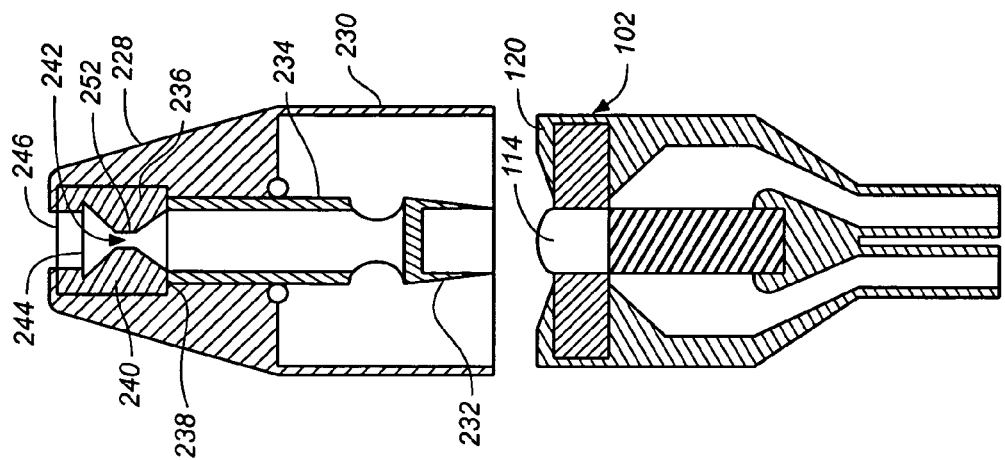
FIG. 13A is a cross-sectional view illustrating a variation of an adapter cap for accessing a valve assembly. The corresponding valve assembly is also shown.

An optional adapter 228 may be provided to allow the operator to electively access the valve assembly 102. In one variation the access adapter 228 comprises a housing 230 with a protruding element 232 for depressing the plunger 114 in the valve assembly 102. In one example, the access adapter 228 comprises a housing 230, supporting a single lumen access cannula 234. An optional valve 236 may be provided at the proximal end 238 of the cannula 234 to prevent fluid backflow from the opened valve assembly 102 and keeping the system sealed when not in use. The valve 236 may include various pliable polymeric materials. In one variation, the valve 236 comprises a block of pliable silicone with a slit to allow needles or wiring to pass through. In another variation, the valve 236 comprises a silicone block 240 with an inner lumen modeled in an hourglass-shape 242 as shown in FIG. 13A. The proximal end 244 of the hourglass lumen is closed. A slit 246 is provided on the closed proximal end 244 to allow an elongated object to be pushed through.

With the access adapter 228 connected to the valve assembly 102, the operator may insert a needle on a syringe through the valve 236 and inject fluids and/or medication through the opened valve assembly 102. In another application, the access adapter 228 is utilized for over the guidewire insertion of a catheter, as shown in FIG. 13B. The distal end 112 of the valve assembly 102 is attached to the proximal end of a catheter. An access adapter 228 is attached to the proximal end 120 of the valve assembly to depress the plunger 114 and open the valve assembly. The distal end of the catheter may then be inserted over a guidewire that has its proximal portion inserted within a vessel of a patient. The catheter is then advanced forward along the length of the guidewire. Finally, the proximal end 248 of the guidewire 250 passes through the opened valve assembly and then through the valve 236 at the distal end of the access cannula 234. The valve 236 prevents fluids in the catheter lumen from back-flowing out of the proximal end of the access adapter 238.

In applications where an hourglass-valve 236 is utilized as illustrated in FIG. 13B, the neck of the hour glass may provide a seal around circumferential surface of the guidewire 250 and provide added protection to back-flow in addition to the slit 246 at the proximal end. Since the neck 252 of the hourglass 236 valve may be configured with a circumferential inner surface including an inner diameter that is equal or slightly smaller than the outer diameter of the guidewire 250, the neck portion 252 may provide a more even seal around the body of the guidewire 250 than the proximal end slit 246.

Although a single lumen access cannula 234 is illustrated in FIG. 13A, one of ordinary skill in the art would appreciate that a dual lumen access cannula may also be implemented in the access adapter to allow the operator to selectively inject or withdrawal fluids from either of the catheter lumens. In addition, one may modify the single lumen access cannula adapter 228 by removing the valve 236, and attaching a catheter to the proximal end of the cannula housing. In another variation, an extension leg may be provided at the proximal end of the housing for connection to a catheter. The modified access cannula adapter may then be utilized to connect a single lumen catheter to a dual lumen catheter for accessing the two lumens simultaneously.

In another variation of the valve assembly 102, a safety sealing disk 254 is implemented to prevent accidental opening of the valve. The safety disk 254 is configured such that depressing the plunger 114 alone can not open the valve. In this design, the access cannula 110 may depress the plunger 114 and at the same time engage the safety disk 254 to establish an open fluid pathway within the valve assembly 102. In one variation, as shown in FIG. 14A, a first spring 256 positioned at the distal end of the plunger provides spring-loading of the plunger 114. A second spring 258 positioned on the shaft of the plunger 114 between the base 260 of the plunger and the safety disk 254 provides the spring-loading of the safety disk 254. Depending on the design criteria, the thickness of the safety disk 254 may be modified to provide the necessary protection. In this design, if the plunger 114 is depressed without engaging the safety sealing disk 254, the second spring 258 keeps the safety sealing disk 254 in place and prevent premature leakage of fluids. When an access cannula 110 is partially inserted into the valve assembly, as shown in FIG. 14B, the distal tip of the cannula 110 engages both the plunger 114 and the safety sealing disk 254. As the plunger 114 and the safety sealing disk 254 are fully depressed, fluids may then flow out of the lumens 148, 150 of the access cannula 110, through the openings 262, 264 on the safety sealing disk 254, and into the channels 130, 132 in the valve assembly housing 104, as shown in FIG. 14C.

FIG. 14D shows the valve assembly housing 104 viewed from the distal end 112 of the housing. Two extension legs 134, 136 form the two inserts for insertion into a dual lumen catheter. FIG. 14E is a plain view of the safety sealing disk 254. A center opening 266 accommodates the plunger 114; two side openings 262, 264 provide the pathways for fluid pass-through when the safety disk 254 is depressed. FIG. 14F is a side view of the septum 138 which provides the seal around the plunger 114 and the safety sealing disk 254 when the valve is closed. When the valve is accessed by an access cannula 110, the septum 138 provides the seal around the access cannula 110 and guides the safety sealing disk as it displaces toward the distal end of the housing. FIG. 14G is a plain view of the septum 138 viewed form the proximal end down its longitudinal axis.

In another variation, as shown in FIG. 15A, the safety sealing disk 254 is spring-loaded by a spring 268 position along the inner wall 270 of the valve assembly housing 104. The septum 138 comprises a disk-shaped block with an opening 140 to accommodate the plunger 114, as shown in FIG. 15E. FIG. 15F illustrates the side view of the septum 138. The safety disk 254, as shown in FIG. 15C, comprises a center opening 266 to accommodate the plunger 114 and two side channels 262, 264 to allow fluid pass-through when the safety sealing disk 254 is depressed. In this design, if the plunger 114 is accidentally depressed without engaging the safety disk 254, as the plunger advances distally, the inner wall 270 of the safety sealing disk is exposed. However, the presence of the safety sealing disk 254 blocks fluid from flowing into or out of the chambers 126, 128 within the valve assembly 102. The distal end of the access cannula 110 is tapered 272 to facilitate insertion of the tip 274 of the cannula between the plunger 114 and the septum 138. In addition, the tapered profile 272 is also configured to engage the safety sealing disk 254. As shown in FIG. 15D, the inner wall 270 of the center opening 266 of the safety sealing disk 254 is configured with a slanted profile 276 matching the tapered profile 272 on the distal end of the access cannula 110. When the access cannula 110 is inserted into the valve assembly 102, the tapered profile 272 on the outer wall of the access cannula 110 engages the inner wall 270 of the safety sealing disk's center opening 266 and forces the safety sealing disk 254 to displace distally, as shown in FIG. 15B. Consequently, fluid paths are established through the valve assembly.

Although in the above examples, a dual channel valve assembly is used to illustrate the functionality of a plunger-based valve assembly, one of ordinary skill in the art having the benefit of this disclosure would appreciate that the plunger-based valve assembly may be modified to accommodate single channel connections or connections with three or more fluid channels. For example, the device shown in FIG. 15B may be modified such that the access cannula 110 has a single lumen and the extension legs 134, 136 at the distal end of the housing may be merged into a single extension. As such, the valve assembly unit may serve as a proximal end protection for a single lumen catheter, and at the same time, provide an interface for connecting another single lumen catheter to serve as an extension. In another variation, the device shown in FIG. 15B may also be modified such that the access cannula 110 supports three or more lumens with corresponding side ports. The valve assembly 102 may be configured with a plurality of chambers matching the number of lumens in the access cannula. As such, the valve assembly may be utilized to provide proximal end protection and connection to a catheter including a plurality of lumens. In another variation, the valve assembly may be utilized for sealing a plurality of single lumen catheters and allow simultaneous access of all the single lumen catheters connected to the valve assembly. For example, the valve assembly may have four chambers with four corresponding ports. Each of the ports is connected to a separate catheter. An access cannula including four lumens may then be utilized to access the four catheters connected to the four chamber valve assembly simultaneously.

In yet another aspect of the invention, a valve assembly 102 is configured for single lumen catheter connection and access protection. The valve assembly comprises a housing which is accessible at the proximal end 180 with an access cannula 110 including a slightly tapered 282 blunt end 284, as shown in FIG. 16A. A catheter 292 may be attached (either pre-connected or attachable) to the distal end of the valve assembly housing 294. An access tubing 286 with a closed proximal end 288, and one or more side orifices 290 for accessing the lumen of the tubing 286 is positioned at the center of the housing 290. The distal end 296 of the access tubing is attached to the valve assembly housing 294 and a fluid communication path is established between the lumen of the catheter 292 and the lumen of the access tubing 286. In one design, the access tubing 286 has two oval shaped orifices 290, 296, as shown in FIG. 16D and FIG. 16E.

A compressible seal 298 is positioned within the valve assembly housing 294 and surrounds the access tubing 286 to seal the orifices 290, 296 on the access tubing 286, as shown in FIG. 16B. The compressible seal 298 may comprise various compressible polymeric materials (e.g., low durometer silicone, closed cell foam rubber, etc.). FIG. 16F is a proximal end view of the compressible seal 298. FIG. 16G is a side view of the compressible seal 298. Indentations 300 are provided around the circumferential surface of the compressible seal 298, such that the compressible seal may have room 302 for displacement within the valve assembly housing 294 when the access cannula 110 engages the valve assembly 102. To provide access to the catheter, the access cannula 110 is aligned with the access tubing 286 within the valve assembly housing 294, and then the access cannula 110 is inserted into the valve assembly 102 and over the access tubing 286. As the access cannula 110 is advanced into the valve assembly 102, as shown in FIG. 16C, the access cannula 110 separates the compressible seal 298 from the access tubing 288 and pushes the compressible seal 298 against the inner wall 304 of the valve assembly housing 294. Because the inner diameter 306 of the access cannula 110 is larger than the outer diameter 308 of the access tubing 286, a fluid flow-path is established between the inner lumen of the access tubing 286 and the inner lumen of the access cannula 110, through the orifices 290, 296 on the inner tubing 286. The distal end 284 of the access cannula 110 is tapered and may be configured to provide an additional seal around the base 310 of the access tubing 286.

Figure 17B:
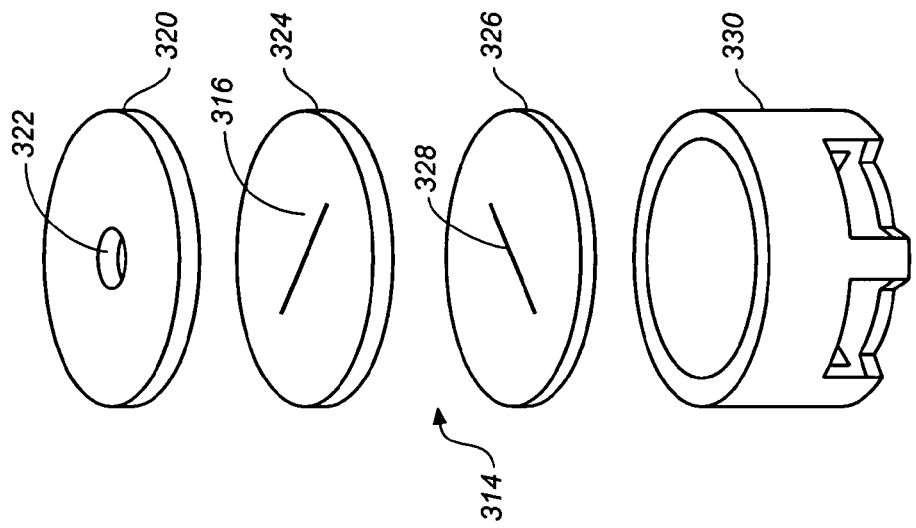
FIG. 17B shows the three polymeric disks and the house chamber of the valve assembly of FIG. 17A in a disassembled condition.
Figure 17A:
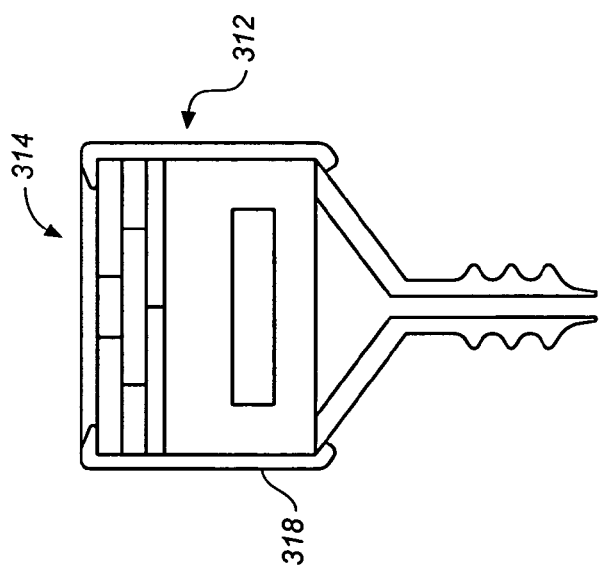
FIG. 17A illustrates another variation of a single lumen catheter connector with a valve assembly comprising a plurality of polymeric disks layered one over the other.

In another variation, a single lumen catheter connection 312 is configured with a valve assembly 314 comprising a plurality of polymeric layers, each with at least one access slit 316. In the example shown in FIG. 17A, the valve assembly comprises a housing 318 supporting three layers of a disk, which may be made of silicone, layered over each other to form the access port 312. The top layer 320 has an opening 322 at the center of the disk to guide the placement of an access cannula, as shown in FIG. 17B. The middle layer 324 has a slit 316 across the center of the disk. The bottom layer 326 also has a slit 328 on the center of the disk. An inner frame 330 is provided to support the polymeric disks. The middle 324 and the bottom disk 326 are positioned such that their corresponding slits 316, 328 are angularly aligned with each other. In one variation, the two slits 316, 328 are positioned perpendicularly with each other such that the slits cross at the center of the access port. One of ordinary skill in the art would appreciate that three or more polymer disks with slits may also be implemented. Additional disks with circular openings may be implemented as the base layer or between the slit disks to keep the access cannula aligned when it is inserted in to the valve assembly.

Figure 18B:
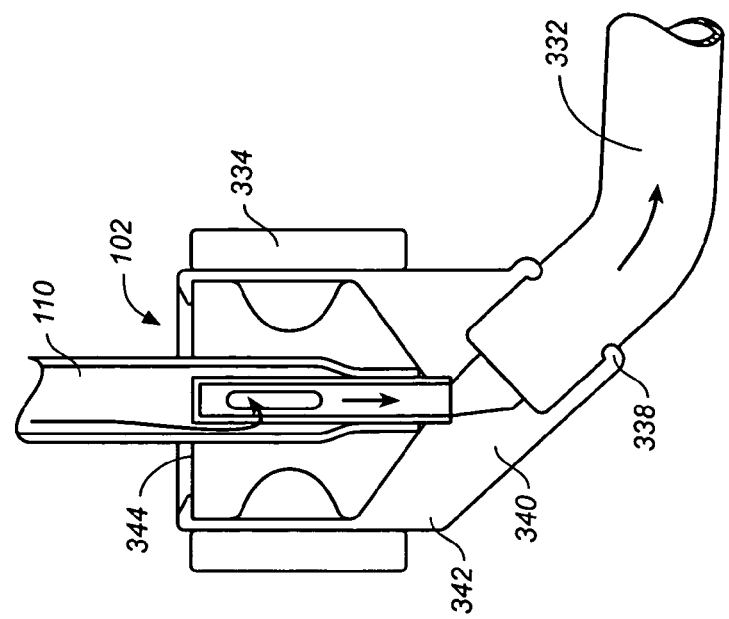
FIG. 18B illustrates the access cannula engaging the valve assembly of FIG. 17A. The valve is shown in an opened position to allow fluid flow.
Figure 18A:
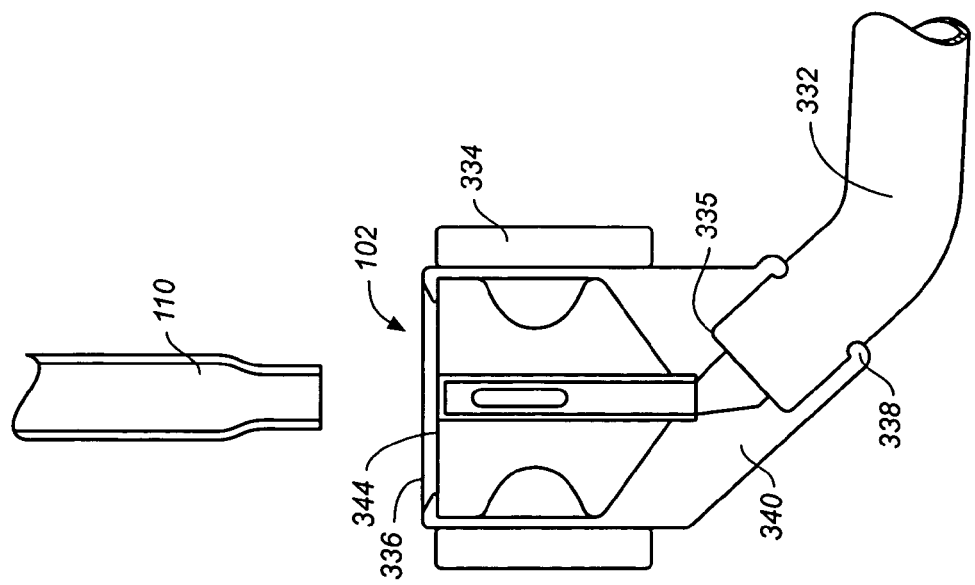
FIG. 18A is a cross-sectional view illustrating another variation of a catheter valve assembly implanted under the skin of a patient. The corresponding access cannula is also shown.

The various valve assemblies described above may be configured to serve as needle-less catheter access systems. In one example, illustrated in FIG. 18A, the valve assembly 102 is attached to the proximal end 335 of a catheter 332 and implanted into a patient's body. The outer circumference of the valve assembly may be encased within a Vitacuff® material 334 to facilitate tissue in-growth to seal around the valve assembly 102 implanted under the skin of the patient. The proximal access end 336 of the valve assembly 102 is exposed on the surface of the skin. The distal end 338 of the valve assembly housing 342 may be modified to provide suitable catheter connection angles depending on the particular application. For example, in FIG. 18A, the distal portion 340 of the valve assembly housing 342 has a bent profile to support that attachment of a catheter 332 at an angle. To access the implanted catheter 332, an access cannula 110 is inserted into the valve assembly 102 through the access port 344 exposed on the surface of the skin. FIG. 18B shows the access cannula 110 engaging the valve assembly 102 and a fluid path is established between the lumen of the implanted catheter 332 and the lumen of the access cannula 110. Although, in FIGS. 18A and 18B, a single lumen catheter connection is illustrated, one of ordinary skill in the art having the benefit of this disclosure would appreciate that other valve assemblies disclosed herein, whether including one, two or three lumens/chambers, may also be implemented as an access port for an implanted catheter.

Furthermore, the various valve assemblies described herein, whether integrated within the proximal end of a catheter or as a separate adapter, may be configured with an antithrombogenic agent and/or an antibacterial agent. An antithrombogenic agents or material may be placed inside the lumen of the valve assembly to prevent coagulation and formation of thrombus within the valve assembly. For example, an antithrombogenic agent (e.g., heparinized hydrophilic polymer, various heparin complexes, etc.) may be coated on the inner surface of the adapter's lumens/chambers. In another variation, an antibacterial agent or material may be placed within the lumen/chamber of the valve assembly to serve as a bacterial barrier to prevent migration of infective agents into the lumen of an implanted catheter. For example, the valve assembly housing may comprise of an antibacterial polymer. In another variation, the inner lumen/chamber of the valve assembly may be coated with an antibacterial agent (e.g., polymer integrated with antibiotic such as gentamicin, nitrofurazone, Minocycline-rifampin, etc.). In anther variation, the valve (e.g., polymeric duckbill valve, spring-loaded plunger, etc.)

within the valve assembly comprises a polymer impregnated with an antithrombogenic and/or an antibacterial agent. Furthermore, an antibacterial agent may also be provided on the outer surface of the valve assembly housing.

In view of the disclosure herein, one of ordinary skill in the art would appreciate that a catheter device incorporating the valve assembly described herein may be utilized in various medical procedures. One of ordinary skill in the art would also appreciate that catheters including integrated valve assemblies described herein may be inserted into the patient's circulatory system through various veins and arteries with procedures that are well known to one of ordinary skill in the art.

In one example, the following devices and instruments are prepared for carrying out an implant procedure: multi-lumen catheter tube, introducer needle, multiple tear away sheath dilator introducers, J-flex guidewires, trocars, lock right adapters with clamps, injection caps, scalpel, sutures, and adhesive wound dressing. Additionally, the physician is also be provided with scissors, forceps, needles dishes, syringes and gauze. In particular approach, the catheter with a valve assembly incorporated at the proximal end is inserted into a patient's jugular vein. The procedure begins with placing the patient in a position with the patient's head turned to the opposite side of where catheter tip is to be placed into the jugular vein. The anatomical landmark for proper insertion is defined by the triangle formed by the lateral edge of the sternal head, the medial edge of the clavicular head of the sternocleidomastoid muscle, and the upper edge of the clavicle. The patient's neck and a portion of the patient's thorax beneath the clavicle, at least about 20 cm, are prepared for incision. Thereafter, the patient is draped and a local anesthetic is administered.

A local anesthetic skin wheel may be created, taking care to infiltrate the subcutaneous tissue for about 2 to 3 cm. Next, with an 18-gauge needle attached to a syringe, the physician can identify the internal jugular vein by aspiration and then proceed at an angle while continuing to aspirate with the syringe. Once the internal jugular vein has been located, the method includes detaching the syringe while leaving the needle in place. Thereafter the J-flex guidewire is introduced through the needle and into the internal jugular vein. The guidewire is passed with minimal resistance into the desired location. The needle is removed, leaving the guidewire in place. The tip of the guidewire rests at the junction of the superior vena cava and the right atrium. Appropriate guidewire placement may be confirmed with fluoroscopy.

Next, with a scalpel, the physician makes an incision in the skin that is wide enough for the catheter tube to pass. A tearaway sheath dilator may be introduced over the guidewire and into the vein far enough to dilate the vessel. After expanding the vein wall, the guidewire may be removed. A trocar is screwed onto the catheter tube. The dilator may be removed, leaving the tearaway sheath in place to introduce the catheter tube. As the catheter tube is fed into the sheath the tearaway sheath may be torn away. Fluoroscopy may then be performed to confirm catheter tube placement. The distal tip with the venous lumen opening on the dual lumen dialysis catheter is positioned at the opening of the right atrium, and the arterial lumen opening, proximal to the distal tip, is positioned approximately 4 cm higher. Positioning, as described, may prevent blood recirculation during hemodialysis. Next, a tunnel, of about 8 to 10 cm, is created in a caudal and internal direction by means of the tunneler, which may be shaped to physician's preference. The proximal portion of the catheter tube is gently pulled through the tunnel until the loop at the original puncture site is gone. The catheter tube is then adjusted to rest over the clavicle.

If the catheter implanted has a built-in valve assembly within the lumens of the catheter, an extension leg unit may then be attached to the proximal end of the implanted catheter through the valve assembly. As the extension leg unit is attached to the proximal end of the implanted catheter, the lumen inserts from the extension leg unit or the access cannula engages the valve assembly located within the proximal end of the implanted catheter. In another variation, after tunneling the proximal end of the catheter, a removable valve assembly may be connected to the proximal end of the implanted catheter. An access cannula may then be inserted into the valve assembly to access the implanted catheter.

For dialysis application, the arterial-line and the venous-line on the dialysis machine may be connected to the extension leg unit or the access cannula prior to attaching the extension leg unit or the access cannula to the valve assembly on the catheter. When an extension leg unit is utilized, the luer connector on the extension leg unit may be back-fitted over the shaft of the implanted catheter. Next, the compression sleeve may be backfitted over the catheter shaft. The two lumen inserts are positioned within the implanted catheter's two lumens, respectively, creating a friction fit. Optionally, proper markings may be provided on the valve assembly and the extension leg unit (or the access cannula unit), so that the arterial and venous lines from the hemodialysis machine can be connected to withdraw and infuse blood from the appropriate lumen in the implanted hemodialysis catheter.

In applications where tunneling is required, the physician may attach the tunneler to the distal end of the catheter. The catheter may then be tunneled from the exit incision site to the cut-down site before inserting the distal end of the catheter into the body. However, for catheter implementing an extension leg unit with a removable bifurcate or a detachable valve assembly, the physician may be removed the bifurcate or the detachable valve assembly so that the proximal end of the catheter can be easily reverse tunneled. In this case, the proximal portion of the catheter is tunneled from the cut-down site to the exit incision site. Optionally, a tunneler including an interconnector or locking mechanism matching the locking interface at the proximal end of catheter may be utilized for tunneling of the catheter. For example, the proximal end of a multi-lumen catheter with a built-in valve assembly may have a threading 34 surrounding the body of the catheter, as shown in FIG. 1 (left). One may provide a tunneler including a connector with matching threads, for the tunneling procedure. The physician screws the proximal end of the multi-lumen catheter onto the connector at the proximal end of the tunneler to secure the catheter to the tunneler. Once the proximal portion of the multi-lumen catheter is tunneled through the tissue, the tunneler is then removed, and the corresponding extension leg unit may be inserted into the proximal end of the catheter. In another variation, tunneling devices with other attachment mechanisms that are capable of holding/gripping onto the proximal end of the catheter may also be utilized to complete the tunneling of the catheter.

This invention has been described and specific examples of the invention have been portrayed. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent that there are variations of the invention, which are within the spirit of the disclosure or equivalent to the inventions found in the claims, it is the intent that this patent will cover those variations as well. Finally, all publications and patent applications cited in this specification are herein incorporated by reference in their entirety as if each individual publication or patent application were specifically and individually put forth herein.

What is claimed as new and desired to be protected by Letters Patent of the United States is:

1. A catheter device, comprising:
   a catheter valve assembly comprising a valve positioned in each of a, plurality of lumens and a first coupling interface; and
   an extension leg unit comprising a second coupling interface configured to mate with the first coupling interface, a third coupling interface positioned about a proximal portion of at least one of a plurality of extension legs, and a plurality of lumen inserts, each lumen insert in fluid communication with a lumen of one of the extension legs, the lumen inserts configured to open the valves when the extension leg unit is connected to the catheter valve assembly.

2. The catheter device according to claim 1, the catheter valve assembly further comprising a catheter including a plurality of lumens, wherein the valves and first coupling interface are positioned at a proximal portion of the catheter.

3. The catheter device according to claim 2, the extension leg unit further comprising an extension tubing connected to each of the extension legs.

4. The catheter device according to claim 1, further comprising a catheter extending from a distal end of the catheter valve assembly.

5. The catheter device according to claim 4, wherein the catheter valve assembly is integrated in the catheter.

6. The catheter device according to claim 4, the catheter comprising a plurality of lumens.

7. The catheter device according to claim 1, the valve comprising a unidirectional valve.

8. The catheter device according to claim 1, each of the plurality of extension legs in fluid communication with a corresponding lumen insert of the plurality of lumen inserts.

9. The catheter device according to claim 1, wherein each of the plurality of lumen inserts is configured to contact and force open at least one of the valves when the extension leg unit is connected to the catheter valve assembly.

10. The catheter device according to claim 9, wherein the first and second coupling interfaces are configured for interlocking connection to each other.

11. The catheter device according to claim 10, the first and second coupling interfaces respectively comprising a male and a female luer connection.

12. The catheter device according to claim 9, further comprising a catheter including a plurality of lumens and extending from the distal end of the catheter valve assembly.

13. The catheter device according to claim 12, further comprising a plurality of extension tubings, wherein each of the plurality of extension tubings is connected to one of the plurality of extension legs on the extension leg unit.

14. The catheter device according to claim 12, each of the plurality of valves comprising a duck-bill valve.

15. The catheter device according to claim 12, each of the plurality of valves comprising a bi-leaf valve.

16. The catheter device according to claim 12, each of the plurality of valves comprising a spring-loaded valve.

17. The catheter device according to claim 12, each of the plurality of valves comprising a unidirectional valve.

18. The catheter device according to claim 12, wherein the cross-sectional area of the catheter valve assembly is approximately equivalent to the cross-sectional area of a longitudinal mid-point of the catheter.

19. A catheter assembly comprising:
   an elongated tubing including a plurality of lumens;
   a plurality of valves, each of the plurality of lumens including a valve positioned at a proximal end of the lumen; and
   a fluid interconnector comprising a plurality of lumen inserts extending from the distal end of the fluid interconnector, each of the lumen inserts being configured to insert into a proximal portion of one of the plurality of lumens, the plurality of lumen inserts being further configured to engage the plurality of valves and force the valves open when the lumen inserts are positioned inside the lumens, the plurality of valves remaining closed when the lumen inserts are removed.

20. The catheter assembly according to claim 19, the fluid interconnector further comprising a plurality of branches, each of the plurality of branches supporting a fluid pathway to one of the plurality of lumen inserts.

21. The catheter assembly according to claim 20, further comprising a plurality of extension tubings, each of the branches being connected to one of the plurality of extension tubings.

22. The catheter assembly according to claim 21, each of the valves comprising a bi-leaf valve.

23. The catheter assembly according to claim 20, each of the plurality of valves comprising an unidirectional valve.

24. The catheter assembly according to claim 20, the elongated tubing including two lumens, each of the lumens including a valve, and the fluid interconnector comprising two lumen inserts and two branches.

25. The catheter assembly according to claim 24, further comprising a coupling lock that detachably locks the distal end of the fluid interconnector to the proximal end of the elongated tubing.

26. The catheter assembly according to claim 24, each of the valves comprising a duck-bill valve.

27. The catheter assembly according to claim 24, each of the catheter lumens including a D-shaped cross-section.

28. The catheter assembly according to claim 27, each of the valves comprising a unidirectional valve.

29. The catheter assembly according to claim 20, further comprising a pair of corresponding locking interfaces integrated on the proximal end of the elongated tubing and the distal end of the fluid interconnector for connecting the interconnector with the elongated tubing.

30. The catheter assembly according to claim 20, wherein the catheter is configured to support a flow rate of at least 200 ml/min in each of the lumens.

31. The catheter assembly according to claim 20, wherein the catheter is configured to support a flow rate of at least 400 ml/min in each of the lumens.

32. The catheter assembly according to claim 20, further comprising a porous mesh or filter positioned within at least one of the fluid pathways.

33. The catheter assembly according to claim 20, the fluid interconnector further comprising a porous mesh or filter positioned within at least one of the plurality of branches.

34. The catheter assembly according to claim 19, each of the valves comprising a unidirectional valve.

35. The catheter assembly according to claim 19, wherein the catheter is configured to permit insertion of an introducer through one of the catheter lumens.

36. The catheter assembly according to claim 19, wherein the proximal end of the catheter is configured with a profile that allows reverse tunneling of the catheter.

37. The catheter assembly according to claim 19, wherein the distal end of the interconnector is configured as a male luer interface for connection to a proximal end of the elongated tubing.

38. The catheter assembly according to claim 19, wherein the plurality of valves prevents retrograde flow through the catheter.

* * * * *